US012728017B2

(12) United States Patent
Carter et al.

(10) Patent No.: US 12,728,017 B2
(45) Date of Patent: Sep. 8, 2026

(54) SYSTEMS AND METHODS FOR JOINT BALANCING

(71) Applicant: Mako Surgical Corp., Weston, FL (US)

(72) Inventors: Matthew Carter, Auckland (NZ); Matthew L. Walker, Remuera (NZ); Xiangyi Liu, Mahwah, NJ (US); Azhar Ali, West Orange, NJ (US); Daniele De Massari, Eindhoven (NL); Thies Wuestemann, Freiburg (DE); Sietske Witvoet, Delfgauw (NL); Emily Hampp, Far Hills, NJ (US); Jason Karl Otto, Sioux Falls, SD (US); Kelly Dunn, Burlington, VT (US); Kevin Bechtold, Davie, FL (US); Jenna Lyon, Sydney (AU)

(73) Assignee: Mako Surgical Corp., Weston, FL (US)

( * ) Notice: Subject to any disclaimer, the term of this patent is extended or adjusted under 35 U.S.C. 154(b) by 1100 days.

(21) Appl. No.: 17/387,510

(22) Filed: Jul. 28, 2021

(65) Prior Publication Data

US 2022/0031473 A1 Feb. 3, 2022

Related U.S. Application Data

(60) Provisional application No. 63/057,657, filed on Jul. 28, 2020.

(51) Int. Cl.
*A61F 2/46* (2006.01)
*A61B 17/16* (2006.01)
(Continued)

(52) U.S. Cl.
CPC .......... *A61F 2/461* (2013.01); *A61B 17/1675* (2013.01); *G16H 20/40* (2018.01);
(Continued)

(58) Field of Classification Search
CPC .............. A61F 2/461; A61F 2002/4633; A61F 2002/4662; A61F 2002/4668; A61F 2/38;
(Continued)

(56) References Cited

U.S. PATENT DOCUMENTS 4,484,975 A 11/1984 McElroy
6,205,411 B1 3/2001 DiGioia, III et al.
(Continued)

FOREIGN PATENT DOCUMENTS

EP 3278757 A2 2/2018
EP 3524200 A2 8/2019

OTHER PUBLICATIONS

International Search Report issued for Appln. No. PCT/US2021/043505 mailed Dec. 30, 2021.
(Continued)

*Primary Examiner* — Jennifer Robertson
*Assistant Examiner* — Elina Sohyun Jang
(74) *Attorney, Agent, or Firm* — Lerner David LLP

(57) ABSTRACT

Disclosed herein is a balancer algorithm to perform joint balancing calculations to identify target solutions based on surgeon preference. The balancer algorithm can generate a suggested final implant plan from a predetermined range. The balancer algorithm can be used in a knee arthroplasty procedure to generate bone resection depths, bone gaps, implant angulations, required soft tissue release, etc. Input to the balancer algorithm can include preoperative data, intra-operative data, and surgeon preference data.

19 Claims, 23 Drawing Sheets

(51) Int. Cl.

| | |
|---|---|
| ***G16H 20/40*** | (2018.01) |
| ***G16H 40/20*** | (2018.01) |
| ***G16H 50/20*** | (2018.01) |
| ***G16H 50/30*** | (2018.01) |
| ***G16H 50/70*** | (2018.01) |
| ***G16H 70/20*** | (2018.01) |
| ***G16H 70/60*** | (2018.01) |

(52) U.S. Cl.
CPC ............. *G16H 50/70* (2018.01); *G16H 70/20* (2018.01); *G16H 70/60* (2018.01); *A61F 2002/4633* (2013.01); *A61F 2002/4662* (2013.01); *A61F 2002/4668* (2013.01); *G16H 40/20* (2018.01); *G16H 50/20* (2018.01); *G16H 50/30* (2018.01)

(58) Field of Classification Search
CPC .......... A61B 17/1675; A61B 2034/102; A61B 34/10; A61B 2034/105; A61B 2034/108; G16H 20/40; G16H 50/70; G16H 70/20; G16H 70/60; G16H 40/20; G16H 50/20; G16H 50/30
See application file for complete search history.

(56) References Cited

U.S. PATENT DOCUMENTS

| | | | |
|---|---|---|---|
| 7,094,241 | B2 | 8/2006 | Hodorek et al. |
| 8,126,533 | B2 | 2/2012 | Lavallee |
| 8,241,016 | B2 | 8/2012 | Laufer et al. |
| 8,257,360 | B2 | 9/2012 | Richard et al. |
| 8,611,504 | B2 | 12/2013 | Kubiak et al. |
| 8,617,171 | B2 | 12/2013 | Park et al. |
| 8,721,568 | B2 | 5/2014 | Rock et al. |
| 8,990,052 | B2 | 3/2015 | Lavallee et al. |
| 9,129,054 | B2 | 9/2015 | Nawana et al. |
| 9,220,571 | B2 | 12/2015 | Lavallee |
| 9,532,845 | B1 | 1/2017 | Dossett et al. |
| 9,597,096 | B2 | 3/2017 | Aghazadeh |
| 9,649,119 | B2 | 5/2017 | Rock et al. |
| 9,684,768 | B2 | 6/2017 | Lavallee et al. |
| 9,901,463 | B2 | 2/2018 | Mahfouz |
| 9,913,690 | B2 | 3/2018 | Grimm et al. |
| 9,955,983 | B2 | 5/2018 | Aghazadeh |
| 10,136,952 | B2 | 11/2018 | Couture et al. |
| 10,198,968 | B2 | 2/2019 | Imhauser et al. |
| 10,226,302 | B2 | 3/2019 | Lacal et al. |
| 10,285,683 | B2 | 5/2019 | Plaskos et al. |
| 10,321,904 | B2 | 6/2019 | Plaskos et al. |
| 10,342,621 | B2 | 7/2019 | Dossett et al. |
| 10,383,578 | B2 | 8/2019 | Branch et al. |
| 10,383,638 | B2 | 8/2019 | Cheal et al. |
| 10,402,517 | B2 | 9/2019 | Sett et al. |
| 10,441,437 | B2 | 10/2019 | Lavallee |
| 10,842,570 | B2 | 11/2020 | Grimm et al. |
| 10,932,855 | B2 | 3/2021 | Shupe et al. |
| 10,952,753 | B2 | 3/2021 | McAuliffe et al. |
| 2005/0119661 | A1 | 6/2005 | Hodgson et al. |
| 2005/0234332 | A1 | 10/2005 | Murphy |
| 2007/0233267 | A1 | 10/2007 | Amirouche et al. |
| 2010/0010506 | A1 | 1/2010 | Murphy |
| 2010/0081971 | A1* | 4/2010 | Allison ..................... A61F 7/00 606/1 |
| 2012/0209394 | A1* | 8/2012 | Bojarski ............... A61F 2/4202 623/18.11 |
| 2014/0135791 | A1 | 5/2014 | Nikou et al. |
| 2014/0324403 | A1* | 10/2014 | Gotte ........................ A61F 2/46 703/2 |
| 2015/0106024 | A1 | 4/2015 | Lightcap et al. |
| 2017/0065350 | A1* | 3/2017 | Dossett .................. G16H 20/40 |
| 2017/0071671 | A1 | 3/2017 | Neumann et al. |
| 2017/0245872 | A1 | 8/2017 | Rock et al. |
| 2017/0265944 | A1 | 9/2017 | Shupe et al. |
| 2017/0340389 | A1 | 11/2017 | Otto et al. |
| 2017/0347945 | A1 | 12/2017 | Branch et al. |
| 2017/0347962 | A1 | 12/2017 | Branch et al. |
| 2017/0360512 | A1* | 12/2017 | Couture ................. A61B 34/30 |
| 2018/0033338 | A1 | 2/2018 | Iannotti et al. |
| 2018/0132949 | A1* | 5/2018 | Merette ................... G06T 11/60 |
| 2018/0140232 | A1 | 5/2018 | Fleig et al. |
| 2018/0185107 | A1 | 7/2018 | Nikou et al. |
| 2018/0233222 | A1 | 8/2018 | Daley et al. |
| 2018/0303564 | A1 | 10/2018 | Nikou et al. |
| 2018/0344414 | A1 | 12/2018 | Nikou et al. |
| 2019/0008501 | A1 | 1/2019 | Plaskos et al. |
| 2019/0133700 | A1 | 5/2019 | Nikou et al. |
| 2019/0133701 | A1 | 5/2019 | Nikou et al. |
| 2019/0151031 | A1 | 5/2019 | Lacal et al. |
| 2019/0172373 | A1 | 6/2019 | Imhauser et al. |
| 2019/0183411 | A1 | 6/2019 | Yildirim et al. |
| 2019/0240045 | A1 | 8/2019 | Couture |
| 2020/0000400 | A1 | 1/2020 | McKinnon et al. |
| 2020/0138518 | A1 | 5/2020 | Lang |

OTHER PUBLICATIONS

Extended European Search Report including Search Opinion from 21851253.1, dated Jun. 16, 2024, pp. 1-8.

* cited by examiner

216

| Flexion Angle | Max Med Gap | Max Lat Gap |
|---|---|---|
| 0° | 23.0 mm | 23.3 mm |
| 10° | 23.1 mm | 23.2 mm |
| 20° | 23.3 mm | 24.1 mm |
| 45° | 24.0 mm | 24.1 mm |
| 90° | 26.5 mm | 27.3 mm |

| | Planning DOF | Example Values |
|---|---|---|
| Tibia | Insert Thickness | 9, 10, 11, 12 |
| | Slope | 1, 2, 3 |
| | Valgus-Varus | -1.0, -0.5, 0, 0.5, 1.0 |
| | External Rotation | -1, 0, 1, 2, 3, 4, 5 |
| Femur | SI translation | -2, -1, 0, 1, 2 |
| | AP translation | -1, -0.5, 0, 0.5, 1.0 |
| | Flexion | 0, 1, 2, 3, 4, 5 |
| | Valgus-Varus | -3, -2, -1, 0, 1, 2, 3 |
| | External Rotation | -1, 0, 1, 2, 3, 4, 5 |

FIG. 14

FIG. 17
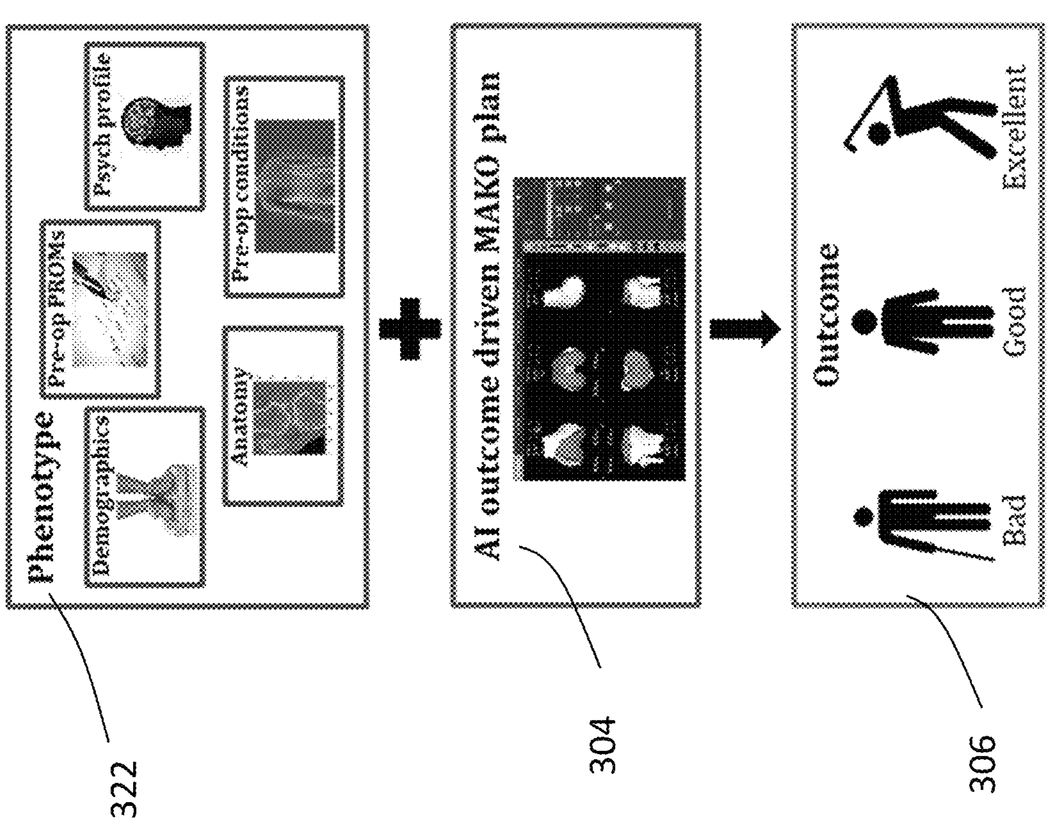
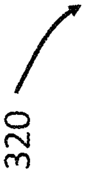

330
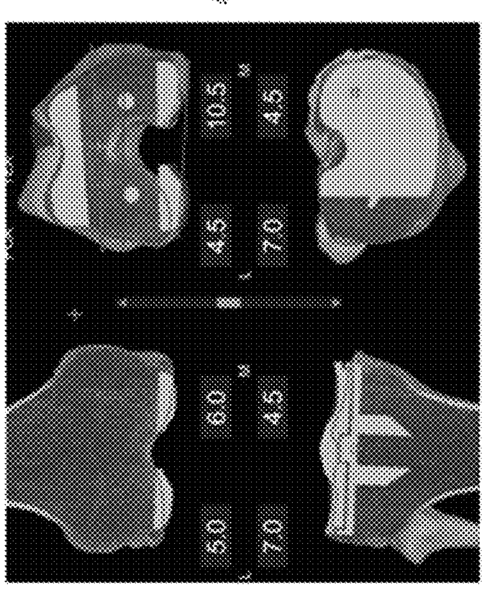
FIG. 21
329
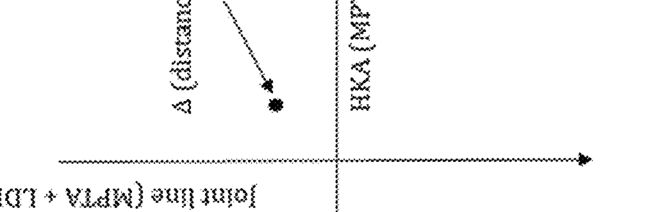
FIG. 20

332

| Table | Variable | Label |
|---|---|---|
| Surgical plan | Femoral valgus/varus | A |
| | Femoral internal/external rotation | B |
| | Femoral flexion/extension | C |
| | Tibial valgus/varus | D |
| | Tibial external/internal | E |
| | Tibial slope | F |
| | Femoral distal resection delta = Femoral medial distal resection depth – Femoral lateral distal resection depth | G |
| | Femoral posterior resection delta = Femoral medial posterior resection depth – Femoral lateral posterior resection depth | H |
| | Tibial resection delta = Tibial lateral resection depth - Tibial medial resection depth | I |

FIG. 22

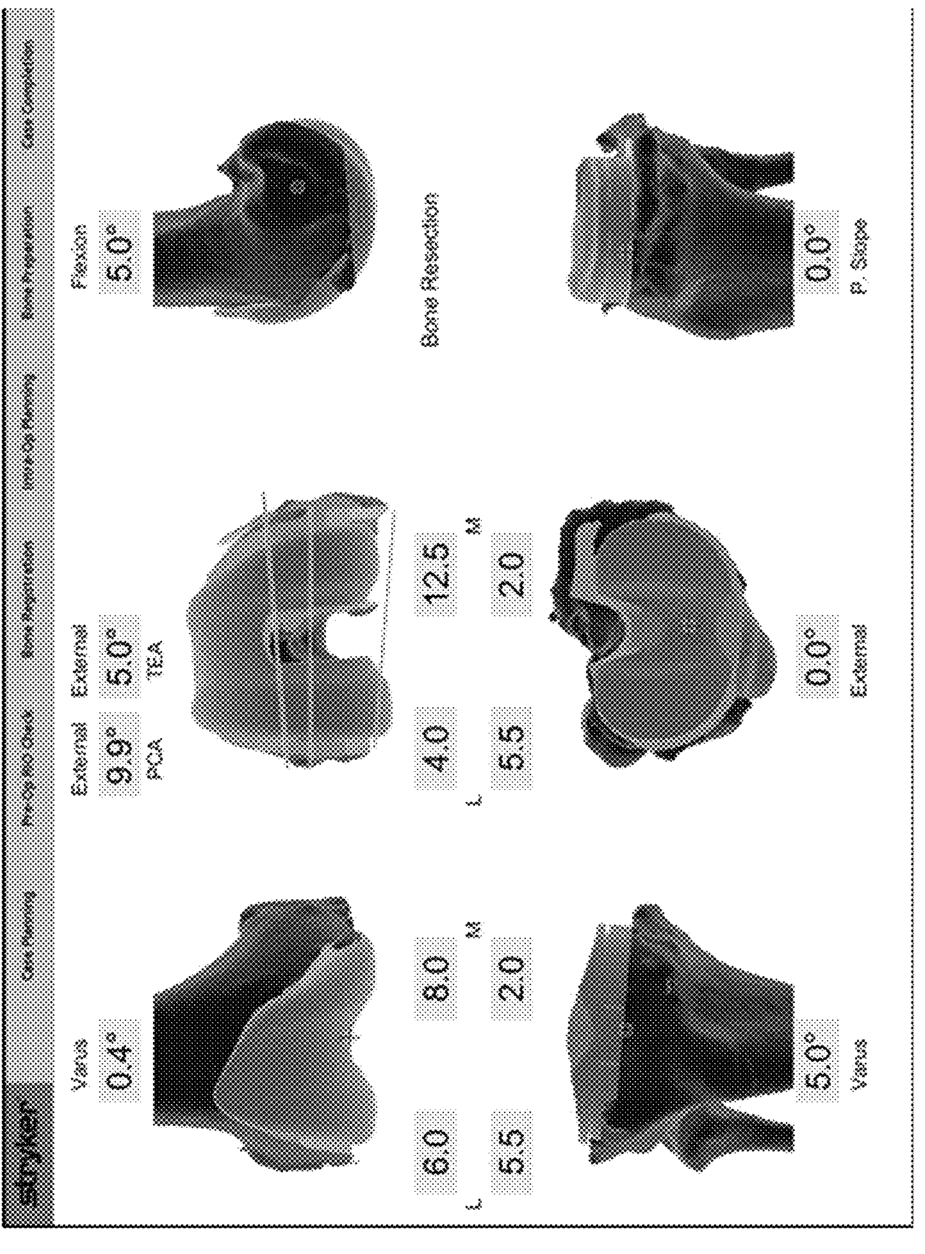
FIG. 23
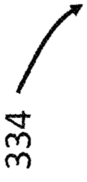

SYSTEMS AND METHODS FOR JOINT BALANCING

CROSS-REFERENCE TO RELATED APPLICATIONS

This application claims the benefit of the filing date of U.S. Provisional Patent Application No. 63/057,657 filed Jul. 28, 2020, the disclosure of which is hereby incorporated herein by reference.

FIELD OF THE DISCLOSURE

The present disclosure relates to a system and a method for performing orthopedic procedures, and in particular to a system and a method for performing joint replacement procedures.

BACKGROUND OF THE DISCLOSURE

Joint replacement procedures generally include replacing a subject's joint with prosthetic joint components. For example, a total knee arthroplasty ("TKA") procedure includes replacement of the distal end of the femur and the proximal end of the tibia with a femoral prosthesis and a tibial prosthesis, respectively. Multiple bone resections on the distal femur and the proximal tibia are required prior to the implantations of these prostheses. Proper soft-tissue tension, joint alignment and balance are necessary for smooth and well-aligned joint movement.

A surgeon may need to intraoperatively perform multiple calculations utilizing various joint measurements to identify proper implant sizes and placement of same. Changing any one of the input variables would require multiple new calculations to identify a proper solution.

Thus, improved systems and methods for performing joint replacement procedures are desired.

BRIEF SUMMARY OF THE DISCLOSURE

In certain embodiments, the present disclosure relates generally to a balancer algorithm configured to perform joint balancing calculations and to identify a target solution based on surgeon preference. The balancing algorithm may generate a suggested final implant plan from a predetermined range.

In an aspect of the present disclosure, a method for determining resection depths for a knee arthroplasty procedure is provided. A method according to this aspect may include the steps of selecting targeted postoperative knee data including targeted resection depths for the femur and the tibia; determining a plurality of planned resection depths that may be within the targeted resection depth ranges based on preoperative knee data and intraoperative knee data, and selecting final resection depths for the femur and the tibia from the plurality of planned resection depths. The final resection depths may be within the targeted resection depths.

Continuing in accordance with this aspect, the final resection depths may include a final distal medial femoral resection depth, a final distal lateral femoral resection depth, a final posterior medial femoral resection depth, and a final posterior lateral femoral resection depth. The final resection depths may include a final medial tibial resection depth, and a final proximal lateral tibial resection depth. The preoperative knee data may include initial femoral and tibial resection depths. The initial femoral and tibial resection depths may include an initial distal medial femoral resection depth, an initial distal lateral femoral resection depth, an initial posterior medial femoral resection depth, and an initial posterior lateral femoral resection depth. The initial femoral tibial resection depths may include an initial medial tibial resection depth, and an initial proximal lateral tibial resection depth. The preoperative knee data may include an initial femoral component angulation and rotation. The preoperative knee data may include an initial tibial component angulation. The preoperative knee data may include initial medial and lateral extension gaps. The preoperative knee data may include initial coronal limb extension (HKA) and flexion angles.

Continuing in accordance with this aspect, the targeted postoperative knee data may include a targeted postoperative femoral component angulation range and a targeted postoperative femoral component rotation range. The targeted postoperative knee data may include a targeted postoperative tibial component angulation range. The targeted postoperative knee data may include targeted postoperative medial and lateral extension gap ranges. The targeted postoperative knee data may include targeted postoperative limb extension and flexion angle ranges.

Continuing in accordance with this aspect, the step of determining a plurality of resection depths may include the steps of iteratively calculating medial and lateral extension and flexion gaps falling between the targeted postoperative medial and lateral extension gap ranges, iteratively calculating tibial resection depths falling between the targeted postoperative tibial resection depth ranges, and iteratively calculating a femoral component shift in an anterior and posterior direction.

Continuing in accordance with this aspect, the step of determining final resection depths from the plurality of resection depths may include the step of ranking the plurality of resection depths to identify selected resection depths. The step of ranking the plurality of resection depths may include the step of determining medial epicondylar drifts for each of the plurality of resection depths. The medial epicondylar drifts may be calculated from the femoral component shift. The step of ranking the plurality of resection depths may include the step of determining medial lateral column lengths for each of the plurality of resection depths. The lateral column lengths may be calculated from the initial lateral distal resection depths and the final lateral distal resection depths. The step of ranking the plurality of resection depths may include the step of determining proximity of targeted postoperative tibial component angulation ranges with initial preoperative tibial component angulation ranges. The step of ranking may include the step of determining proximity of targeted postoperative tibial component angulation, femoral component angulation, and femoral component rotation to initial angulations or target angulations.

In a further aspect of the present disclosure, a method of determining knee resection angles for knee arthroplasty is provided. A method according to this aspect may include the steps of providing preoperative knee data; providing intraoperative knee data; providing targeted postoperative knee data, the targeted postoperative knee data may include targeted resection angle ranges; determining a plurality of resection angles based on the preoperative knee data, intraoperative knee data and the targeted postoperative knee data, and determining final resection angles from the plurality of resection angles. The final resection angles may be within the targeted resection angle ranges.

In a further aspect of the present disclosure, a non-transitory computer readable medium having stored thereon instructions for determining knee resection depths for knee arthroplasty comprising executable code which when executed by a hardware processor causes the processor to perform steps is provided. Steps according to this aspect may include, obtaining preoperative knee data from a user interface; obtaining intraoperative knee data from the user interface; obtaining targeted postoperative knee data from the user interface, the targeted postoperative knee data may include targeted resection depth ranges; determining a plurality of resection depths based on the preoperative knee data, intraoperative knee data and the targeted postoperative knee data; determining final resection depths from the plurality of resection depths, wherein the final resection depths are within the targeted resection depth ranges; ranking the plurality of resection depths to identify selected resection depths, and displaying the selected resection depths on a display screen.

In a further aspect of the present disclosure, a method for creating a virtual knee model for knee arthroplasty is provided. A method according to this aspect may include, determining pre-resection knee gaps at a plurality of flexion angles; determining a plurality of joint loads at the plurality of flexion angles, respectively; establishing a correlation between the knee gaps and the joints loads at each flexion angle; generating a virtual model of one or more knee ligaments; calibrating the virtual model at a plurality of simulated flexion angles corresponding to the correlation between the knee gaps and joint loads at each flexion angle.

Continuing in accordance with this aspect, the step of determining joint loads may include a step of using a sensor to load the joint. The step of using a sensor may include a step of loading the joint up to joint-specific soft tissue envelope. The step of loading the joint may include a step of determining joint transition loads.

Continuing in accordance with this aspect, the step of generating a virtual model may include a step of generating virtual models of any of a medial collateral ligament, a lateral collateral ligament, a posterior cruciate ligament, an anterior cruciate ligament, an anterior lateral ligament, a popliteal fibular ligament, a posterior capsule, an iliotibial band, and an oblique popliteal ligament. The step of generating the virtual model may include the step of representing the one or more ligaments as nonlinear springs. Each of the one or more ligaments may be represented as a bundle of nonlinear springs. The step of generating the virtual model may include the step of identifying ligament attachment points and generating the virtual models of each of the one or more ligaments to extend from their respective attachment points. The step of calibrating the virtual model may include the steps of determining simulated knee gaps and simulated joint loads at each simulated flexion angle. A method according to this aspect may further include the step of comparing the simulated knee gaps with the pre- or mid-resection knee gaps. A method according to this aspect may further include the step of comparing the simulated joint loads with the joint loads.

In a further aspect of the present disclosure, a method for performing a knee arthroplasty using a virtual knee model is provided. A method according to this aspect may include the steps of generating a virtual model of one or more knee ligaments; calibrating the virtual model at a plurality of simulated flexion angles corresponding to the correlation between pre-resection knee gaps and joint loads at related flexion angles, and simulating the virtual model at a plurality of flexion angles to determine simulated knee gaps and simulated joint loads.

In a further aspect of the present disclosure, a method for predicting patient-specific knee arthroplasty outcomes is provided. A method according to this aspect may include the steps of determining patient phenotype based on patient-specific pre-operative knee data, patient-specific demographic data, patient-specific clinical data, patient-specific behavioral data, patient-specific psychological profile data, patient-specific activity data and historic patient-reported outcome as well as functional measures; and determining patient-specific knee arthroplasty outcomes based on the patient phenotype.

Continuing with this aspect, the pre-operative knee data may include anatomical measurements. The anatomical measurements may include any of an anatomical hip-knee-ankle angle, a medial proximal tibial angle, and a lateral distal femoral angle. The pre-operative knee data may include any of knee flexion and extension gaps and resection depths. The pre-operative knee data may include patient-specific pre-operative condition. The patient-specific pre-operative condition may include any of a range of motion, a forgotten joint score, a knee injury and osteoarthritis score for joint replacement, patient psychological profile, existing clinical conditions, functional assessment measurements, activity data, and patient-reported pain level.

Continuing with this aspect, the patient-specific demographic data may include any of patient height, weight, and gender. The step of determining patient-specific knee arthroplasty outcomes may include the step of determining the patient phenotype using a machine learning model.

In a further aspect of the present disclosure, a method for locating tibial and femoral components during knee arthroplasty is provided. A method according to this aspect may include the steps of selecting targeted ranges for postoperative tibial and femoral component locations on a knee joint; determining a plurality of planned tibial and femoral component locations that may be within the targeted ranges based on preoperative and intraoperative knee data, wherein the preoperative knee data may include initial tibial and femoral component locations, and identifying final tibial and femoral component locations from the plurality of planned tibial and femoral component locations by ranking the plurality of planned tibial and femoral component locations.

In a further aspect of the present disclosure, a method for performing knee resection cuts is provided. A method according to this embodiment may include the steps of performing an initial tibial cut on a tibia of a knee joint, inserting a tensor into the knee joint, moving the knee joint to 10 degrees flexion, adjusting a tensor to ensure a first medial load and a first lateral load of the knee joint are equal, moving the knee to maximum flexion and measuring a maximum flexion angle at maximum flexion, determining if maximum flexion angle is 0, moving the knee joint to 90 degrees flexion, applying the first medial load and second medial load to the knee joint, determining if medial and lateral gaps at 90 degrees flexion are equal, measuring medial and lateral gaps, and performing femoral resections cuts to obtain measured medial and lateral gaps. The tensor may be configured to measure medial and lateral loads.

In a further aspect of the present disclosure, a method of determining joint gaps for a knee arthroplasty procedure is provided. A method according to this embodiment may include the steps of selecting targeted postoperative knee data, determining a plurality of planned joint gaps that are within the targeted postoperative joint gap ranges based on preoperative knee data and intraoperative knee data, and selecting final joint gaps for a femur and a tibia from the plurality of joint planned gaps. The targeted postoperative knee data may include targeted postoperative joint gaps and joint gap ranges for the femur and the tibia. Each joint gap may be defined as a distance between the femur and the tibia. The final joint gaps may be withing targeted joint gap ranges.

Continuing with this aspect, the step of selecting final joint gaps may be performed in real time in response to any change of the targeted postoperative knee data. The final joint gaps may include a final medial extension joint gap, a final lateral extension joint gap, a final medial flexion joint gap, and a final lateral flexion joint gap. The preoperative knee data may include an initial medial extension joint gap, an initial lateral extension joint gap, an initial medial flexion join gap, and an initial lateral flexion joint gap. The targeted postoperative knee data may include a targeted postoperative medial extension joint gap range, a targeted lateral extension joint gap range, a targeted medial flexion joint gap range, and a targeted lateral flexion joint gap range.

Continuing with this aspect, the preoperative knee data may include an initial femoral component angulation and rotation. The preoperative knee data may include an initial tibial component angulation. The preoperative knee data may include initial limb extension and flexion angles.

In a further aspect of the present disclosure, a method of determining femoral and tibial implant angulations for a knee arthroplasty is provided. A method according to this aspect may include the steps of selecting targeted postoperative knee data, determining a plurality of planned implant angulations that are within a targeted postoperative implant angulation ranges based on preoperative knee data and intraoperative knee data, and selecting final implant angulations from the plurality of planned implant angulations. The implant angulations may include a femoral implant angulation with reference to a femur, and a tibial implant angulation with reference to a tibia. The final implant angulations may be within the targeted postoperative implant angulation ranges.

Continuing with this aspect, the step of selecting final implant angulations may be performed in real time in response to on any change of the targeted postoperative knee data. The final implant angulations may include a final femoral implant angulation, a final femoral implant rotation, and a final tibial implant angulation. The preoperative knee data may include initial femoral and tibial resection depths. The initial femoral and tibial resection depths may include an initial distal medial femoral resection depth, an initial distal lateral femoral resection depth, an initial posterior medial femoral resection depth, and an initial posterior lateral femoral resection depth. The initial femoral tibial resection depths may include an initial medial tibial resection depth, and an initial proximal lateral tibial resection depth.

Continuing with this aspect, the preoperative knee data may include an initial femoral implant angulation and rotation. The preoperative knee data may include an initial tibial implant angulation. The preoperative knee data may include initial medial and lateral extension and flexion gaps. The preoperative knee data may include initial limb extension and flexion angles.

Continuing with this aspect, the targeted postoperative knee data may include a targeted postoperative femoral implant angulation range and a targeted postoperative femoral implant rotation range. The targeted postoperative knee data may include a targeted postoperative tibial implant angulation range. The targeted postoperative knee data may include targeted postoperative medial and lateral extension gap ranges. The targeted postoperative knee data may include targeted postoperative limb extension and flexion angle ranges.

Continuing with this aspect, the step of determining a plurality of planned implant angulations may include the steps of iteratively calculating gaps falling between the targeted postoperative gap ranges, iteratively calculating tibial implant angulations falling between the targeted postoperative tibial angulation ranges, iteratively calculating the femoral resections depths falling between the initial plurality of femoral resection depths, and iteratively calculating a required soft tissue release and a required quadrant for the release.

Continuing with this aspect, the step of determining final implant angulations from the plurality of planned implant angulations may include the step of ranking the plurality of planned implant angulations to identify selected implanted angulations. The step of ranking the plurality of planned implant angulations may include the step of determining medial epicondylar drifts for each of the plurality of planned implant angulations. The medial epicondylar drifts may be calculated from the femoral component shift.

Continuing with this aspect, the targeted postoperative knee data may include required postoperative soft tissue release in a medial extension quadrant, a lateral extension quadrant, a medial flexion quadrant or a lateral flexion quadrant.

In a further aspect of the present disclosure, a method for performing a knee arthroplasty using a virtual knee model is provided. A method according to this aspect may include the steps of generating a virtual model of one or more knee ligaments, calibrating the virtual model at a first simulated flexion angle corresponding to the correlation between pre-resection knee gaps and joint loads at the first flexion angle, and simulating the virtual model at a plurality of flexion angles to determine simulated knee gaps and simulated joint loads.

BRIEF DESCRIPTION OF THE DRAWINGS

A more complete appreciation of the subject matter of the present disclosure and the various advantages thereof may be realized by reference to the following detailed description, in which reference is made to the following accompanying drawings:

FIG. 11 is a table showing flexion angles and corresponding maximum medial and lateral gaps;

FIG. 14 is a table showing design of experiment matrix with tibial and femoral planning parameters;

FIG. 17 is a schematic drawing showing a treatment clustering module of the knee joint alignment outcome prediction model of FIG. 16;

FIG. 20 is a graph showing a correlation between hip-knee-angle and joint line;

FIG. 21 is a schematic view of femoral and tibial components placed on a knee joint;

FIG. 22 is a table showing various joint plan parameters;

FIG. 23 is a schematic view of femoral and tibial components associated with the joint plan parameters of FIG. 22;

DETAILED DESCRIPTION

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "implant trial" and "trial" will be used interchangeably and as such, unless otherwise stated, the explicit use of either term is inclusive of the other term. Similarly, the terms "implant," "component," and "prosthesis" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the invention.

Balancer Algorithm

Figure 1:
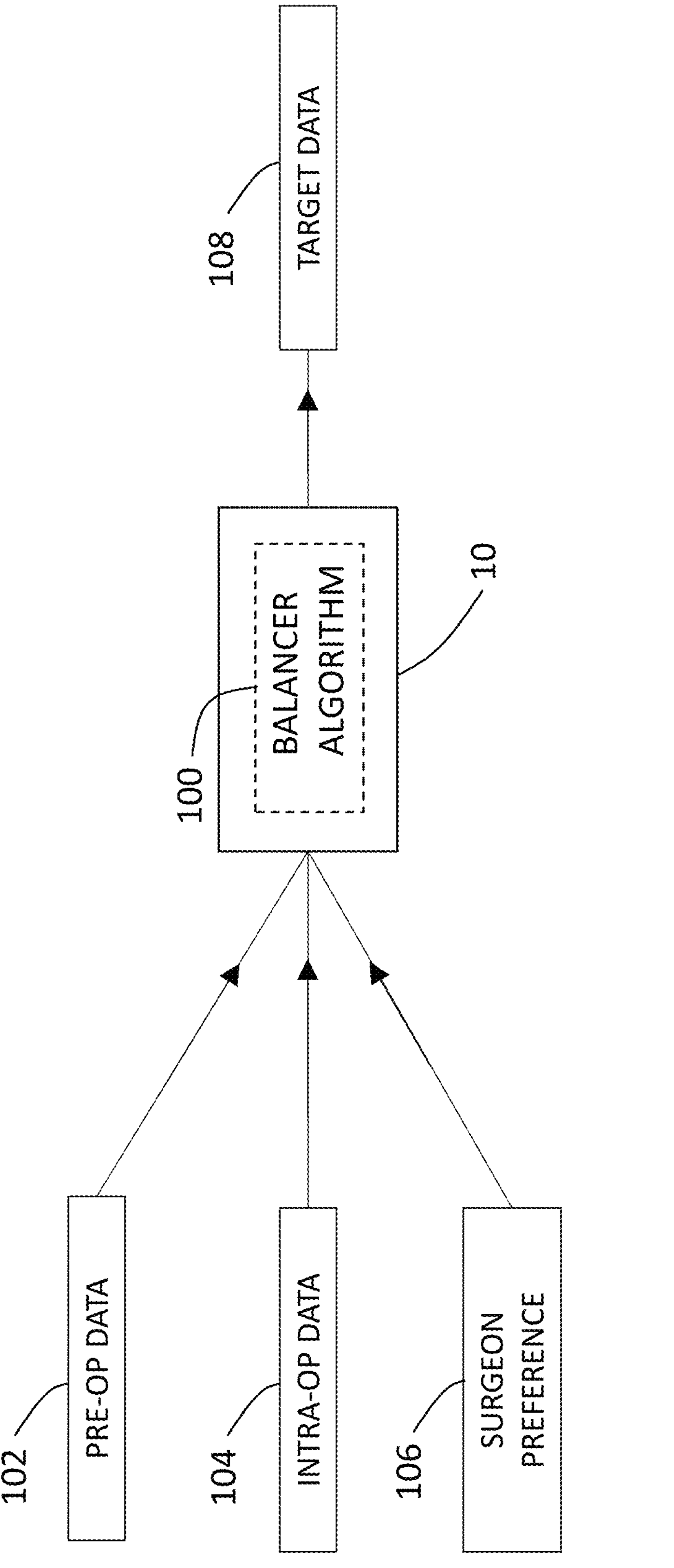
FIG. 1 is a schematic drawing of a balancer algorithm according to a first embodiment of the present disclosure.

FIG. 1 is a schematic drawing of a balancer algorithm 100 of a computing device 10 according to an embodiment of the present disclosure. Computing device 10 can be a cell phone, tablet, computer, or any other device that can be communicatively coupled to balancer algorithm 100. While the balancer algorithm of the present disclosure is generally discussed with reference to a knee surgery, it should be understood that the balancer algorithm can be utilized in any joint procedure conducted manually or robotically or any combination thereof. Input to balancer algorithm 100 includes pre-op data 102, intra-op data 104, and surgeon preference 106. Pre-op data 102 includes all data inputs available prior to commencing the surgical procedure and includes, for example, initial positioning of femoral and tibial components. The initial positioning of femoral and tibial components can be based on anatomical condition of the knee join for the femoral component—i.e., if there is no cartilage wear of the femur, then the femoral component can be placed at predefined distance from the distal and posterior medial and lateral surfaces of the femur. If there is cartilage wear, then the surgeon can make an estimation of the cartilage wear, and the initial femoral and tibial component position are adjusted to replicate the pre-wear anatomical position. Wear can be estimated or measure from a pre-operative image obtained from a CT scan, MRI, ultrasound, x-ray, etc. An operator can collect many of these inputs during patient examinations and enter these values to balancer algorithm 100. Intra-op data 104 includes all data inputs available during the surgical procedure. Each of these input data categories is more fully described below.

Figure 2:
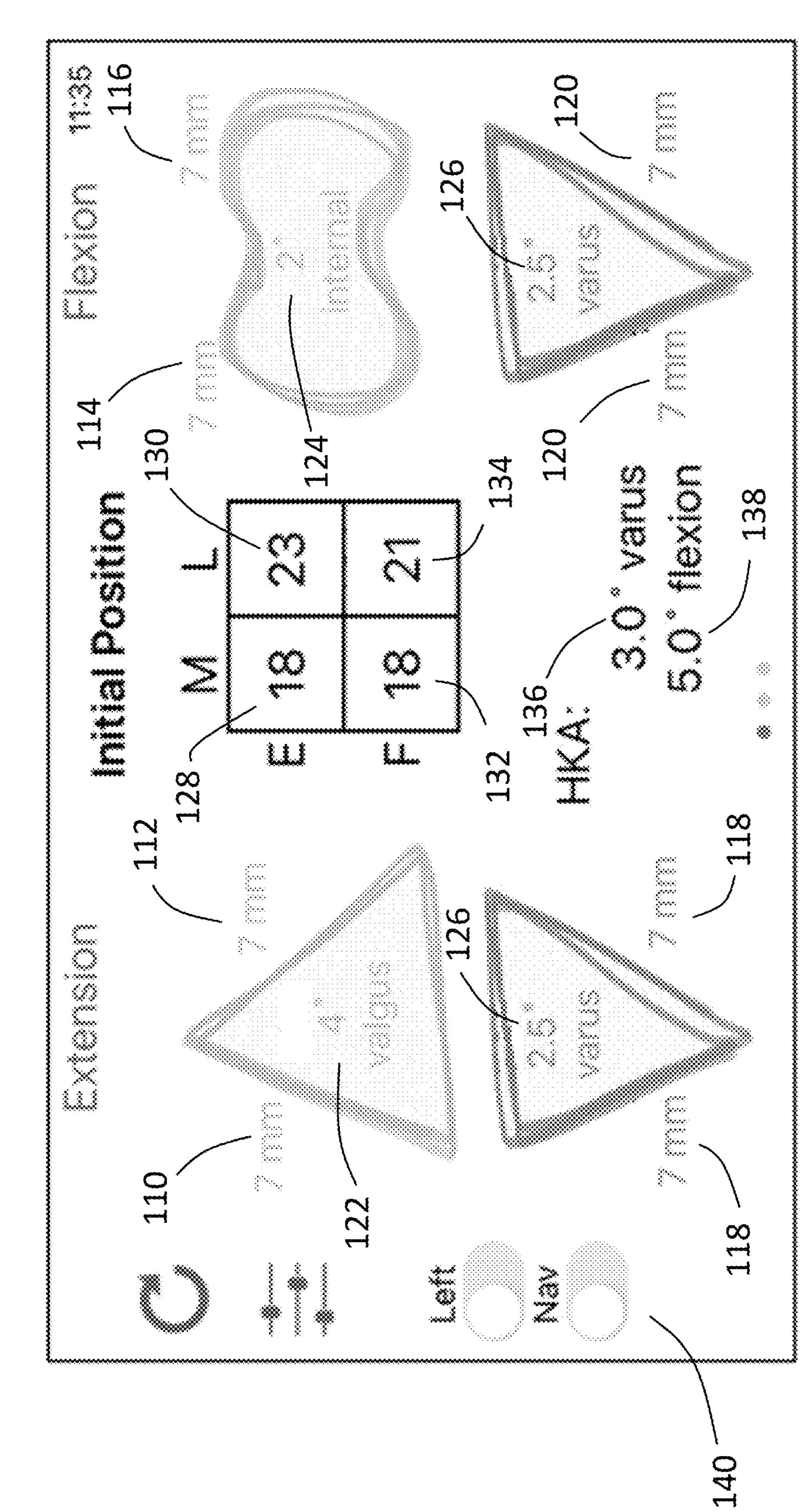
FIG. 2 is a schematic view of an input screen of the balancer algorithm of FIG. 1.

Referring now to FIG. 2, there is shown an input screen 12 of balancer algorithm 100 according to an embodiment of the present disclosure. An operator can input various pre-op data 102 and intra-op data 104 to input screen 12. Pre-op data 102 can include pre-operative plan values, such as technology used, operative side, resection depths and implant alignments. Intra-op data 104 can include initial intra-operative flexion/extension gaps and Hip Knee Angle ("HKA") values. The resection depths for the femur in extension include inputs for a medial distal femoral resection 110 and a lateral distal femoral resection 112. Inputs for a medial posterior femoral resection 114 and a lateral posterior femoral resection 116 are available for the knee joint in flexion. Inputs for the tibial cut include a medial proximal tibial resection 118 in knee extension, and a lateral proximal tibial resection 120 in knee flexion. Resection depth values can be adjusted by an operator by placing a finger in the location of the number and dragging up or down on input screen 12.

Continuing with FIG. 2, input screen 12 includes inputs for the femoral and tibial component angulations. These component angulations can include a femoral component angulation 122 (varus/valgus), a femoral component rotation 124 (internal/external) and a tibial component angulation 126 (varus/valgus). Angulations of the components are displayed on input screen 12 once the correct initial resections have been achieved. The angulation values are adjusted by placing a finger in the location of the image of the component to be adjusted and dragging either left or right. For example, dragging femoral component angulation 122 and tibial component angulation 126 to one side of input screen 12 will cause these values to become more varus, and vice versa if the opposite side is selected. Similarly, an operator can easily change femoral component rotation 124 by dragging the values to right or left side.

Intra-operative data 104 includes limb alignment and maximum stressed gaps in flexion and extension (initial intra-operative gaps) of the knee joint. As shown in FIG. 2, inputs include a medial extension gap 128, a lateral extension gap 130, a medial flexion gap 132, and a lateral flexion gap 134. The maximum stressed gaps can be determined by applying a maximum varus and valgus stress to the limb intra-operatively in flexion and extension. The maximum gaps, which are the distance between the planned initial resections in extension (distal femoral resection values 110, 112 and the proximal tibial resection values 118, 120) and flexion (posterior femoral resection values 114, 116 and the proximal tibial resection values 118, 120. These gaps can be measured once the osteophytes have been removed. An operator can set the initial intra-op gap values by placing a finger in the location of the number to be adjusted and dragging either up or down. Dragging down will decrease the resection value, dragging upwards will increase the gap value.

Inputs for limb alignment values such as HKA 136 and a Fixed Flexion Deformity value ("FFD") 138 can be provided to balancer algorithm 100 via input screen 12. HKA 136 is the overall coronal alignment of the limb in extension (varus/valgus), which can be obtained intra-operatively or pre-operatively by a surgeon holding the limb in extension (0 to 10°) without stress. Other automated calculations to estimate the HKA can also be used. The HKA values are adjusted by placing a finger in the location of the number to be adjusted and dragging either left or right. Dragging to the right side of the screen causes values to become more varus, if the side selected is left, dragging to the left side of the screen will cause the values to become more valgus, if the side selected is left. FFD 138 is the overall sagittal alignment of the limb in extension (hyperextension/fixed flexion), which can be obtained intra-operatively or pre-operatively by the surgeon holding the limb in extension without stress. The FFD values are adjusted by placing a finger in the location of the number to be adjusted and dragging either left or right. Dragging to the right side of the screen will increase the FFD, dragging to the left side of the screen will decrease the FFD. Negative values can denote hyperextension, irrespective of the selected side. Various other features regarding the surgical procedure can be represented and selected via feature 140, which can include navigation options, joint orientation such as operative side (left/right), screen options, etc.

Figure 3:
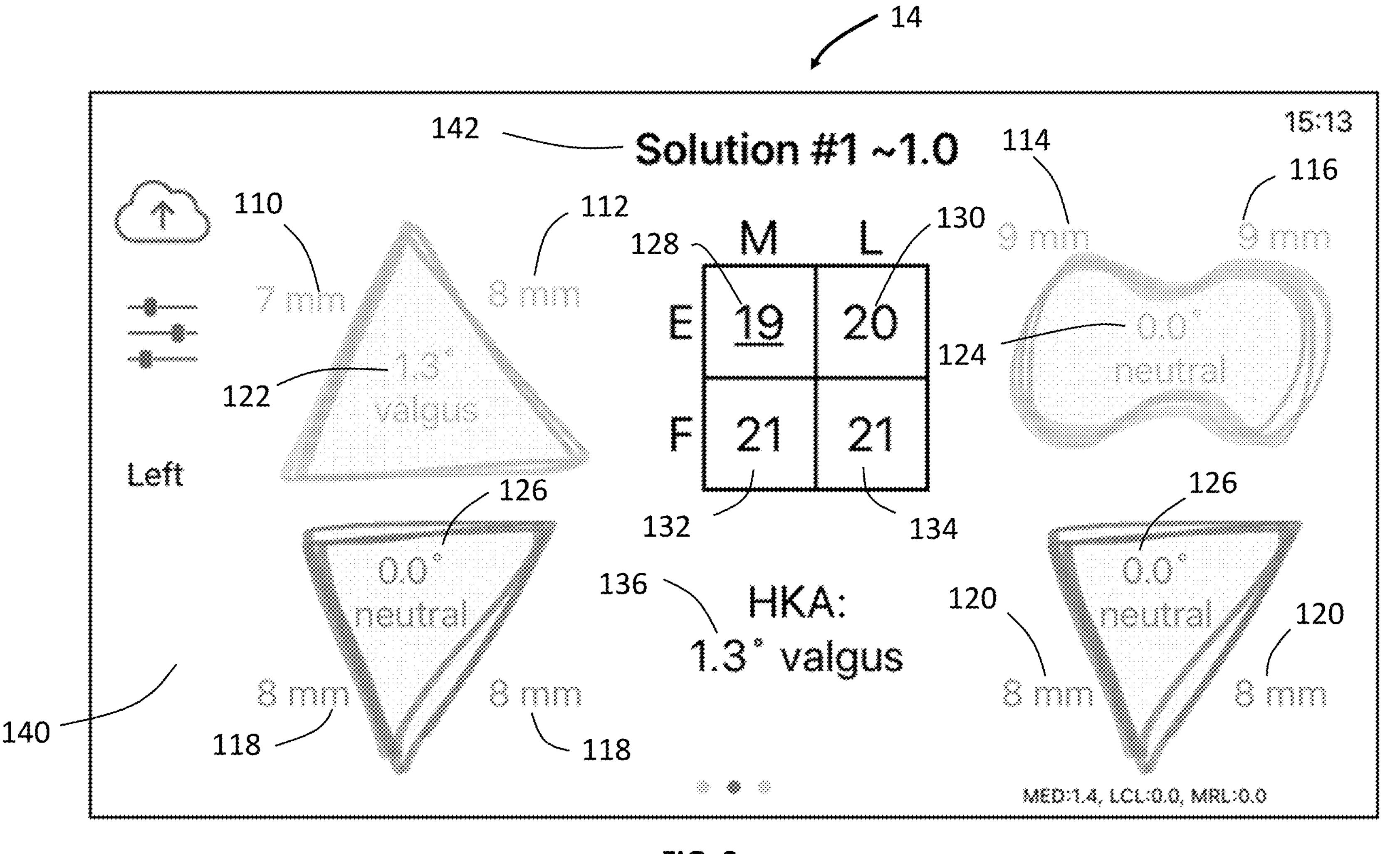
FIG. 3 is a schematic view of a solution screen of the balancer algorithm of FIG. 1.

Referring now to FIG. 3, there is shown a solution screen 14 of balancer algorithm 100 according to an embodiment of the present disclosure. Balancer algorithm 100 iterates all possible implant alignment combinations within set target ranges to solve for the pre-set target gaps. The balancer algorithm presents a list of solutions that meet the criteria in a surgeon preference card 106 which is more fully described below. Balancer algorithm uses a scoring system to identify the most desirable solution from a list can contain hundreds of possibilities. As shown in FIG. 3, balancer algorithm 100 provides the highest ranked solution 142 (lowest score) with all relevant joint parameters discussed above. Additionally, all other solutions are available and can be accessed by an operator by restricting the presented solutions angulations and resections.

Balancer algorithm 100 displays all of the valid solutions that are within the limits set in surgeon preference card 106, in the order of their overall score, lowest to highest. The solution number and score are displayed. The gaps displayed on solution screen 14—medial extension gap 128, lateral extension gap 130, medial flexion gap 132, and lateral flexion gap 134—are the target gaps for the solution. The bone resections (110, 112, 114, 116, 118, 120) and implant angulations (122, 124, 126) displayed are the values that need to be put into a system to achieve the target gaps. HKA value 136 represents the planned HKA with these component angulations.

Any of the displayed values can be adjusted, and in doing so valid solutions are presented that contain the adjusted value. For example, if first solution 142 presented has a tibial component at 5° of varus, but the surgeon feels that that is not appropriate for the patient, then this can be adjusted in real time to a different value. As this value is being adjusted, balancer algorithm 100 presents the solution with the lowest score that contains the adjusted tibial component alignment. If a value is underlined, then it is the only possible value across all of the solutions and cannot be changed. As successive elements of the solution are changed the previous element is locked onto the prior value of same. This allows a surgeon to dial in a set of solutions. For example, from the many hundreds of available solutions, the tibial angulation can be dropped from 5° of varus to 3° of varus depending on the surgeon's preference. Then the medial distal femoral resection will increase a millimeter to 8 mm, leading to corresponding increase in the lateral flexion gap to 22 mm. All remaining solutions would have 3° of tibial varus, 8 mm of medial distal femoral resection and 22 mm of lateral flexion gap, and to show these elements can no longer be changed, they would all be underlined in solution screen 14. This can be reset by moving back to input screen 12 and then back to solution screen 14. Thus, a surgeon can change or modify an implant plan intra-operatively.

Figure 5:
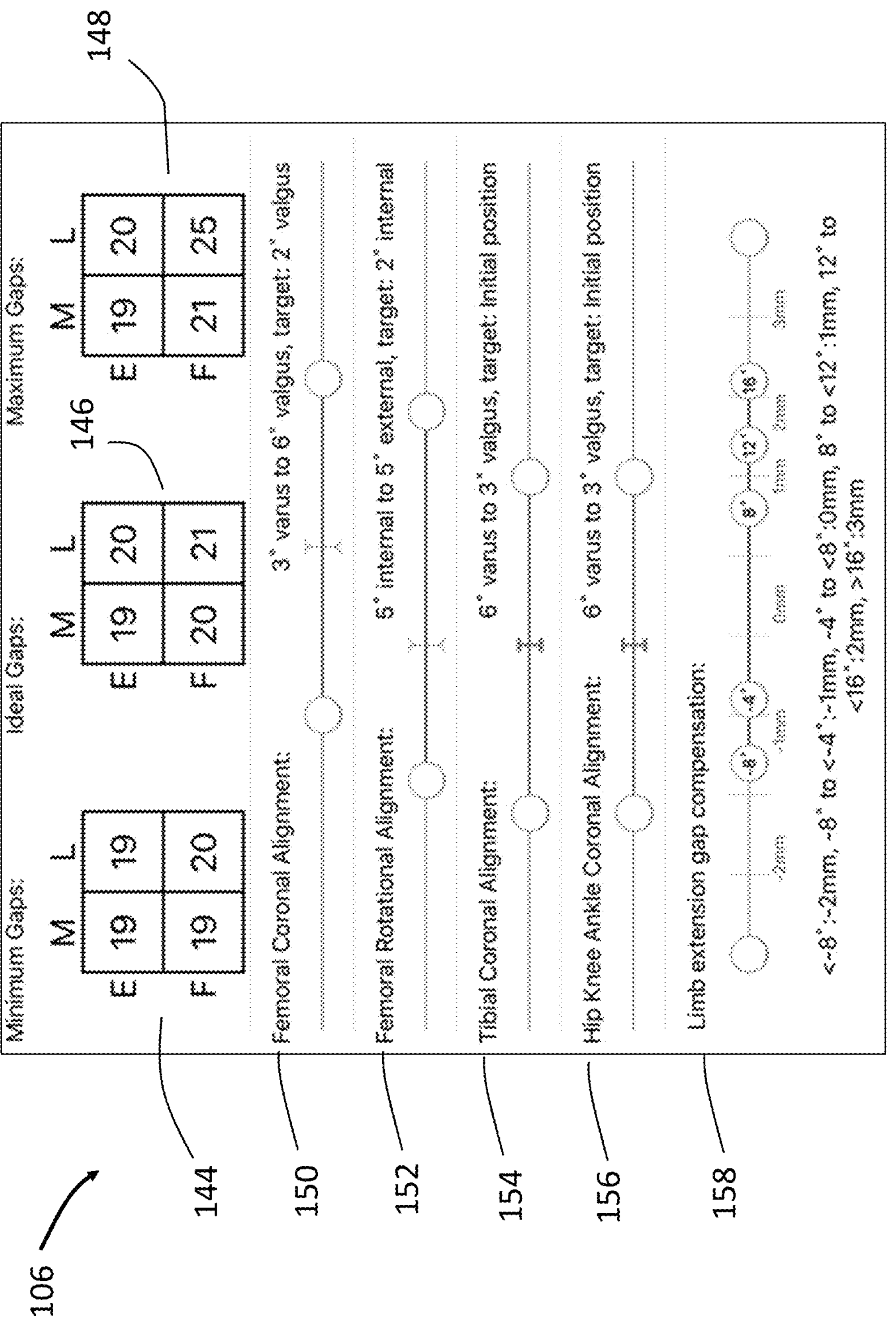
FIG. 5 is a first schematic view of a surgeon preference input of the balancer algorithm of FIG. 1.
Figure 6:
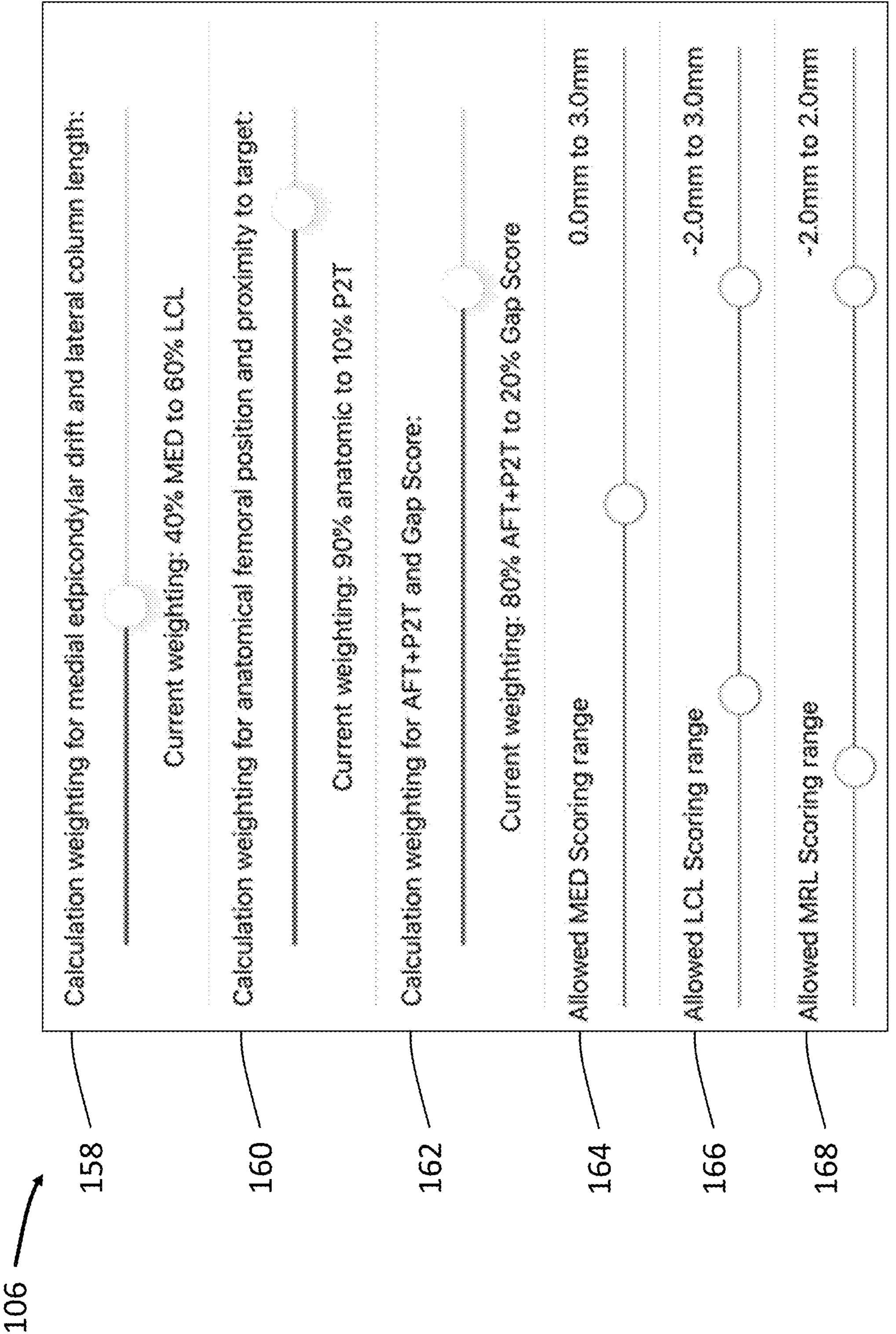
FIG. 6 is a second schematic view of the surgeon preference input of FIG. 5.

FIGS. 5 and 6 show an embodiment of surgeon preference input 106 according to an embodiment of the present disclosure. Surgeon preference input 106 includes minimum gaps 144, ideal gaps 146 and maximum gaps 148. Minimum gaps 144 are target minimum medial and lateral gaps in extension and flexion that the surgeon would accept as a final plan. No solution will be calculated or displayed with gaps tighter than these values. Ideal gaps 146 represent the most desirable targets, but the surgeon may accept solutions within minimum 144 and maximum 148 range of allowable gaps. The surgeon can set ideal medial and lateral extension and flexion gaps. The distance away from the ideal gap is used in the scoring calculation to present gaps that are at or near the ideal gaps before solutions away from the ideal gaps, but still within limits. Maximum gaps 148 represent target maximum medial and lateral extension and flexion gaps that the surgeon would accept as a final plan. No solution will be calculated or displayed with gaps less than these values.

A femoral coronal alignment tool 150 allows the surgeon to set minimum and maximum femoral coronal values (varus/valgus) they would accept as a final implant plan. Two circles can be dragged to set the minimum and maximum. Solutions calculated outside of this range will be displayed in red to show they are outside of set limits. A vertical bar slider adjustment is provided to allow the surgeon to set the target femoral coronal alignment. This target alignment value is used in a Proximity to Target scoring system described below. If doubled tapped this target bar changes to an "I" to represent that the target value is the initial femoral coronal alignment.

A femoral rotational alignment tool 152 allows the surgeon to set the minimum and maximum femoral rotational values (internal/external) they would accept as a final implant plan. Two circles can be dragged to set the minimum and maximum. Solutions will still be calculated and displayed outside of this range, but they will be displayed in red to show they are outside of set limits. A vertical bar can be adjusted and represents the surgeons target femoral rotational alignment. This is target alignment value is used in the Proximity to Target scoring. If doubled tapped this target bar changes to an "I" to represent that the target value is the initial femoral rotational alignment.

A tibial coronal alignment tool 154 allows the surgeon to set the minimum and maximum tibial coronal values (varus/valgus) they would accept as a final implant plan two circles can be dragged to set the minimum and maximum. Solutions will still be calculated and displayed outside of this range, but they will be displayed in red to show they are outside of set limits. The vertical bar can be adjusted and represents the surgeons target tibial coronal alignment. This is target alignment value is used in the Proximity to Target scoring. If double tapped this target bar changes to an "I" to represent that the target value is the initial tibial coronal alignment.

A HKA alignment tool 156 allows the surgeon to set the minimum and maximum HKA values (varus/valgus) they would accept as a final plan. Two circles can be dragged to set the minimum and maximum. Solutions will still be calculated and displayed outside of this range, but they will be displayed in red to show they are outside of set limits. The vertical bar can be adjusted and represents the surgeon's target HKA alignment. This is target alignment value is used in the Proximity to Target scoring. If doubled tapped this target bar changes to an "I" to represent that the target value is the initial hip knee ankle alignment.

A limb extension gap compensation tool 158 is also available in surgeon preference input. Osteo-arthritic knees often have an FFD. The extension gap values need to be recorded in slight flexion as close to the combined femoral flexion and tibial slope as possible. When FFD prevents extending the limb enough to record the extension values at the correct amount of flexion, a suitable compensation via limb extension gap compensation input 158 can be made by the surgeon. This correction is in millimeters and is used to tighten or loosen the recorded extension gap values before balancer algorithm is run.

A weighting tool 158 for scoring between Medial Epicondylar Drift (MED) and Lateral Column Length (LCL) is provided as a sliding scale to set the percentage weighting for MED and LCL. If both are considered equally important then the thumb is moved to the middle of the scale and the weighting is set at 50%. The weighing of one factor is the inverse of the other—i.e., if MED weighting is 20% then LCL weighting is 80%.

A weighting tool 160 for scoring between anatomical femoral position and proximity to target is also provided. These two factors collectively make up the overall score for the solution, which includes an Anatomic Femoral Position ("AFP") and Proximity to Target ("P2T"). The AFP is the weighted combination of the MED and LCL scores. The P2T score is a calculation of how close the femoral and tibial angulation results of the solution are to the targets set in the preferences. The order of the presented solutions can be adjusted to more strongly favor a lower AFP score, or a lower P2T score, depending on preferences by altering the weighting each score has in balancer algorithm 100. This sliding scale is used to set the percentage weighting for AFP and P2T. If both are considered equally important then the thumb is moved to the center of the sliding scale and the weighting is set at 50%. The weighing of one factor is the inverse of the other—i.e., if AFP weighting is 20% then P2T weighting is 80%.

A weighting tool 162 for scoring between the combined AFP and P2T score and a gap score is also provided. The gap score is calculated as the deviation from the ideal gaps, in millimeters. Deviation in the lateral flexion gap greater than the ideal gap is only half counted, as this metric is generally more desirable than any of the other deviations. Alternatively, all four weighting tools described above can be provides in a single weighting tool slider in another embodiment of the present disclosure.

Still further in the surgeon preference input is an allowed MED scoring range tool 168. The allowed MED scoring range tool sets the limits of the acceptable solutions for the calculated MED score. No minimum limit is required as the minimum possible is 0 mm, which is considered ideal. Solutions will still be calculated and displayed outside of this range, but they will be displayed in red to show they are outside of set limits.

An allowed LCL scoring range tool 170 sets the limits of the acceptable solutions for the calculated LCL score. Solutions will still be calculated and displayed outside of this range, but they will be displayed in red to show they are outside of set limits.

An allowed Mid-Range Laxity ("MRL") scoring range tool 172 sets the limits of the acceptable solutions for the calculated MRL score. Solutions will still be calculated and displayed outside of this range, but they will be displayed in red to show they are outside of set limits.

With the above-described inputs from input screen 12 and settings from surgeon preference input 106 balancer algorithm 100 can now be run to output solutions in solution screen 14. Calculations are performed in an iterative loop, to which when three varying parameters are set to a specific value there is only one possible solution calculable. These three varying parameters can be target gaps, tibial component resections, and femoral component shift. Target gaps are an exact set of gaps between minimum gaps 144 and maximum gaps 148 in surgeon preference input 106. Tibial component resections include exact proximal tibial medial and lateral resections that will be used for the solution. The range of this parameter can be about 12° more varus to about 12° more valgus than the initial tibial component alignment. The exact number of possibilities for this parameter is dependent on the resolution set in the inputs. Femoral component shift is a shift that is applied equally to the femoral components anterior/posterior position. As half the scoring is based on femoral position this shift increases the range of femoral positions to ensure the lowest scoring solution is available. The variation in these three parameters set the number of iterations and therefore the number of solutions generated by balancer algorithm 100.

All iterated solutions by balancer algorithm 100 are then allocated a score. The scores are weighted based on the settings in surgeon preference input 106. For score adjustment the weightings are their percentage of 1. At least three factors—AFP, P2T and a target gap score, can be used to compute the overall score for the solution. In another embodiment, at least four factors—MED, LCL, P2T and gap score can be used to compute the overall score for the solution. In yet another embodiment of the present disclosure, the balancer algorithm can be provided with customizable ranking parameters to allow a user to define and prioritize ranking parameters.

There are at least two factors that are necessary for the AFP score—MED and LCL. The MED is a proxy for the concentricity of the medial implant condyle to the femur's anatomical medial condyle. It is calculated via the hypotenuse of the change in distal femoral resection and the change in posterior femoral resection from the initial position to the solution position measured in millimeters. The LCL is the difference between the implants distal lateral point and the anatomical distal lateral point. It is calculated via the change in distal lateral resection from the initial position to the solution position measured in millimeters. The order the solutions are presented in can be altered to more strongly favor a lower MED score, or a lower LCL score, depending on preferences by altering the weighting each score has in balancer algorithm 100. For example, if both are considered equally important, then the weighting can be set at 50%. The weighing of one factor is the inverse of the other—i.e., if MED weighting is 20% then LCL weighting is 80%.

The P2T score is a calculation of how close the solutions femoral and tibial angulations are to the target alignments set in the preferences. The score is the sum of the difference between the solutions component angulation and the set target. A femoral component that is more varus than target is penalized by doubling its score. The femoral component rotation is not scored between 2° internal and 2° external due to high variability in this value. A tibial component that is more valgus than target is penalized by doubling its score. For a patient with an initial HKA alignment in varus, an HKA more valgus than target is penalized by doubling its score. For a patient with an initial HKA alignment in valgus, an HKA more varus than target is penalized by doubling its score. The sum of these four angulation deltas is then converted from degrees to millimeters by dividing by 1.29. In another embodiment, if a femoral component rotation is more valgus than the initial value, a double penalty is applied by balancer algorithm 100. If a femoral component rotation is internal and if the initial value is internal, a double penalty is applied. Similarly, if a femoral component rotation is external and if the initial value is external, a double penalty is applied. If a tibial rotation is more varus than an initial value, a double penalty is applied by balancer algorithm 100.

The target gap score is calculated from the delta between the solutions target gaps and the preference target gaps. Each quadrant is calculated individually, and the score is the sum of these four deltas. The lateral flexion gap delta is reduced by half if it is greater than the target gap, as greater (looser) is more desirable than lower values (tighter). In another embodiment, the lateral flexion gap is not considered for the target gap score, and instead relies on a sum of three deltas.

The MRL score is a calculation of the mathematical difference of the ideal medial implant condyle and the solutions medial implant condyle calculated at 45° flexion. This comes from the mathematical idea that in a balanced solution, proximalising and anteriorising the femoral component by 1 mm, while raising the tibia by 1 mm, will still result in a balanced grid in extension and flexion. However, this may loosen the arc at 45°. Solutions will still be calculated and displayed outside of this range, but they will be displayed in red to show they are outside of set limits. This score is used to filter the solutions, but is not used to order the solutions, therefore a weighting against this score is not required.

Figure 4:
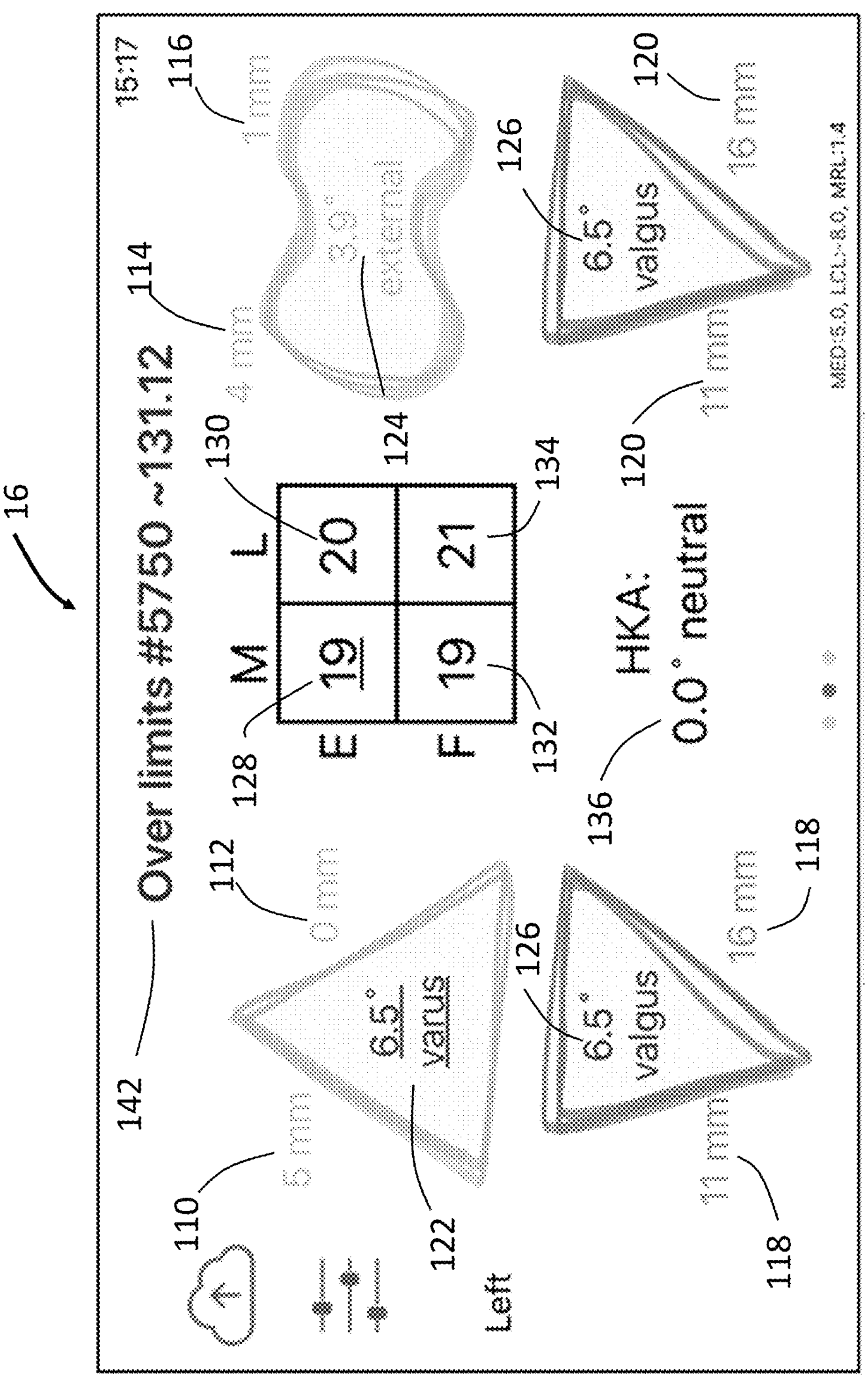
FIG. 4 is a schematic view of a correction screen of the balancer algorithm of FIG. 1.

Referring now to FIG. 4, there is shown a correction screen 16 of balancer algorithm according to an embodiment of the present disclosure. If a solution does not exist within the limits set, then balancer algorithm 100 present a warning via correction screen 16 informing the surgeon of corrective steps. For example, these steps can include providing recommendation to the surgeon for a required amount of soft tissue release, and the quadrant the release can be performed. Balancer algorithm 100 calculates the recommended steps by increasing the initial gaps where they are tight in 1 mm increments, until a solution within the limits is found. It will do this up to a maximum of 10 mm. Thus, balancer algorithm 100 is able to suggest the minimum required soft tissue release that results in a valid solution.

The inputs to the balancer algorithm can be provided manually or automatically via other devices or any combination thereof. The balancer algorithm of the present disclosure can be embedded within or communicatively coupled to a cell phone, tablet, computer, or other electronic device. The balancer algorithm can be used in a manual, navigated, navigated hand-held or navigated robotic procedure. The number and type of inputs accepted by balancer algorithm 100 can also be varied depending on the specific requirements of a particular surgical procedure.

Ligament Modeling

Figure 7:
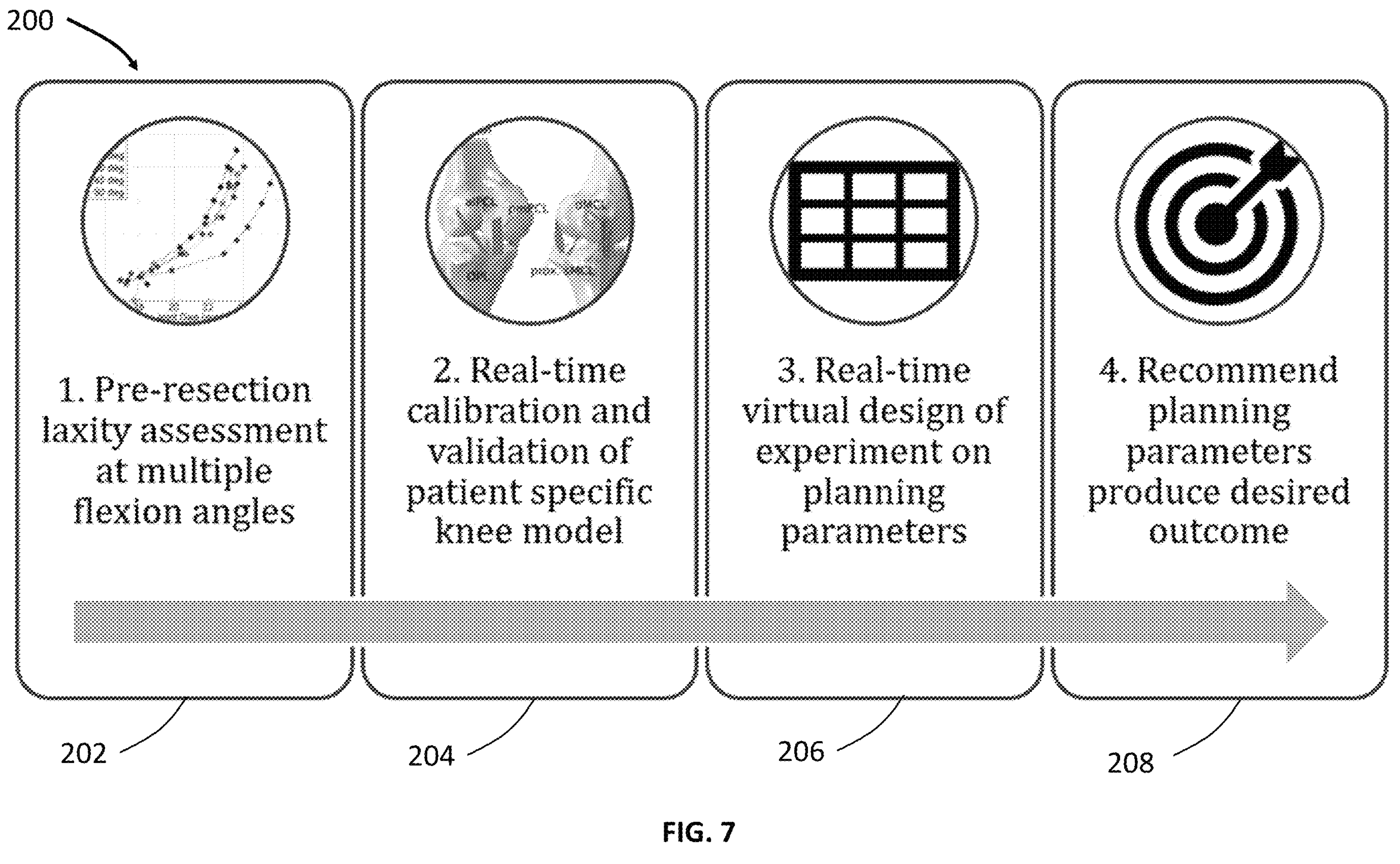
FIG. 7 is a schematic drawing showing the steps for generating a virtual ligament model according to an embodiment of the present disclosure.
Figures 8, 9:
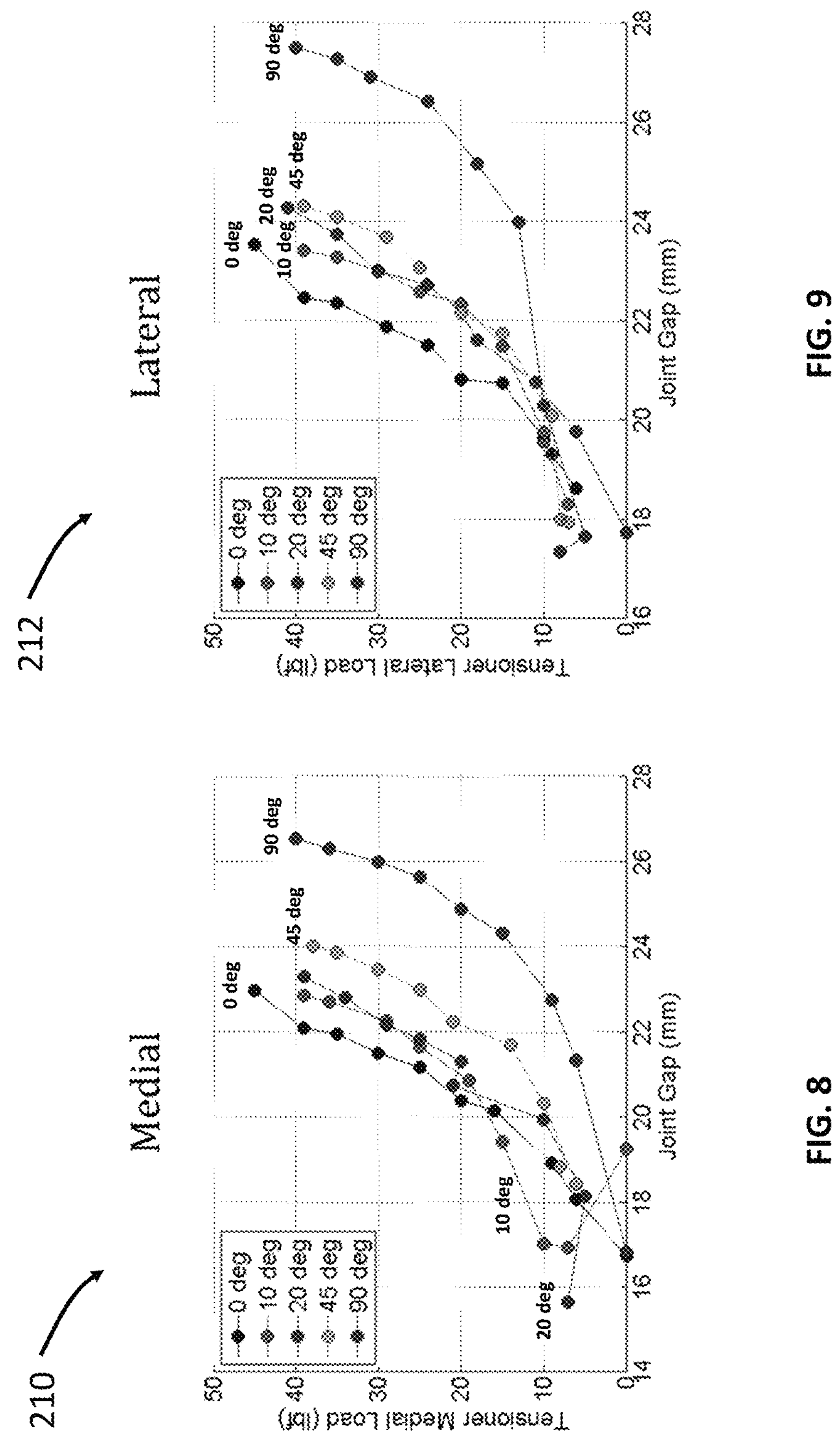
FIG. 8 is a graph showing joint gap versus tensioner load on a medial femur.
FIG. 9 is a graph showing joint gap versus tensioner load of a lateral femur.

FIG. 7 is a schematic drawing showing various steps 200 for generating a virtual ligament model according to an embodiment of the present disclosure. Ligament balancing values, performed either manually or robotically or any combination thereof, are collected at several flexion and extension poses of knee joint. For example, ligament balancing at 0, 45, and 90 degrees flexion can be used for data collection. The ligament balancing data can include bone positions and the loads generated at these positions. A virtual ligament model is created based on ligament attachment points of a specific patient. As shown in FIG. 7, input for the virtual ligament model include data from a pre-resection laxity assessment of a knee joint at multiple flexion angles in step 1 202. The pre-resection laxity assessment and/or surgeon stress test establish patient-specific soft tissue envelope at multiple flexion angles. A sensor or load cell can be placed inside or outside the joint along with kinematics measured using robotic tracker to load the joint up to the patient-specific soft tissue envelope to establish load vs gap curve for each compartment at each flexion angle as shown in graphs depicting medial 210 and lateral 212 joint gap vs. tensioner loads in FIGS. 8 and 9, respectively. Robotic ligament balancing or force measurements can be utilized to generate these graphs. Alternatively, or in conjunction with these graphs, these values can be tabulated in a table 216 shown in FIG. 11 which shows flexion angles corresponding to maximum medial and lateral gaps. The laxity assessment can be conducted manually or with the aid robotic equipment or any combination thereof.

Figure 12:
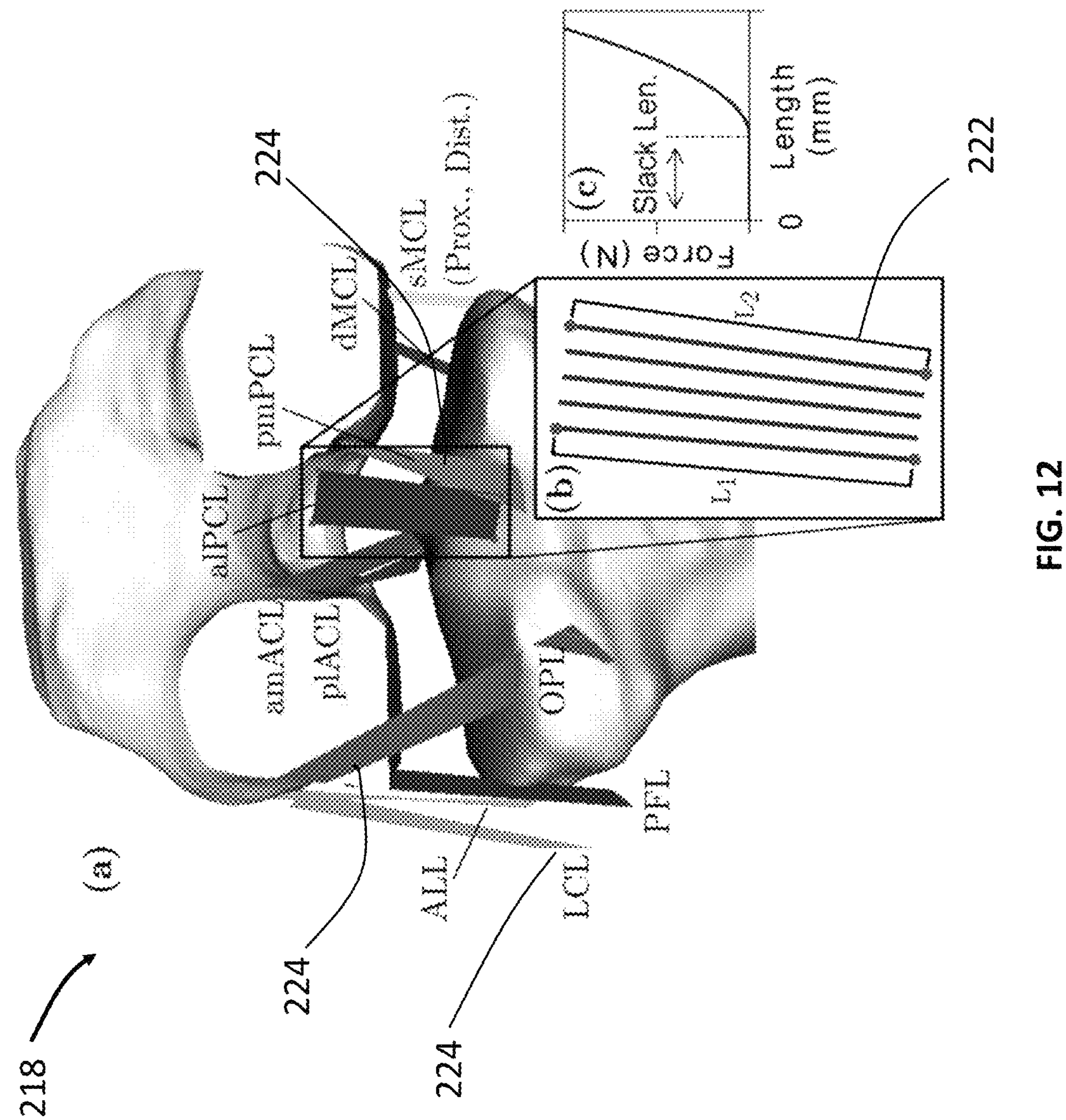
FIG. 12 is a schematic drawing showing a knee joint with the virtual ligaments.

In a step 2 203, a real-time patient specific knee virtual model 218 (FIG. 12) is created from the laxity assessment data gathered from step 1 201. Ligament insertion sites can be identified from imaging such as CT scans, ultrasounds, X-rays, MRI, etc. The virtual ligaments and represented with multiple bundles 222 of nonlinear springs as shown in FIG. 12. All structurally important ligaments 224 can be included such as MCL, LCL, PCL, OPL, etc. A rigid body framework can be used to calibrate ligament properties. At each flexion angle, robotic kinematics are applied to virtual model 218. Ligament properties are optimized until resultant forces match measured loads within a given tolerance for n−1 flexion angles—i.e., 0°, 10°, 20° and 90° laxity curves are used for calibration. Data from one flexion angle is reserved for model validation. For example, 45° laxity curve can used to validate predictability of the model. Thus, a single pose of step 1 202 is used to confirm the output of the model is correct (for example, at 45 deg). If validation of virtual model 218 is confirmed, virtual model 218 is now calibrated and the system can proceed to a next step 206. However, if validation is unsuccessful, step 1 202 can be repeated to acquire additional data. The trained virtual model 218 can now include various implant position options to display the same. This data can be preset based upon mechanical alignment, anatomical alignment, surgeon preferences, etc. A simulation for various combinations of implant positions can now be successfully completed on calibrated virtual model 218. Output from these simulations can include various implant performance metrics including the loads for each implant position. Alternatively, balancer algorithm 100 can be utilized to generate input data. In other embodiments, input data can originate from historical records from other procedures.

A surgeon can now receive a display of the expected simulated loads for various implant positions. The load ranges can be color coded to preferred values. Ideal positions are selected and displayed. The surgeon can then adjust the plan and see how the loads would vary with the changes to the positions. A display illustrating each solution can be presented to a surgeon for evaluation.

Figure 10:
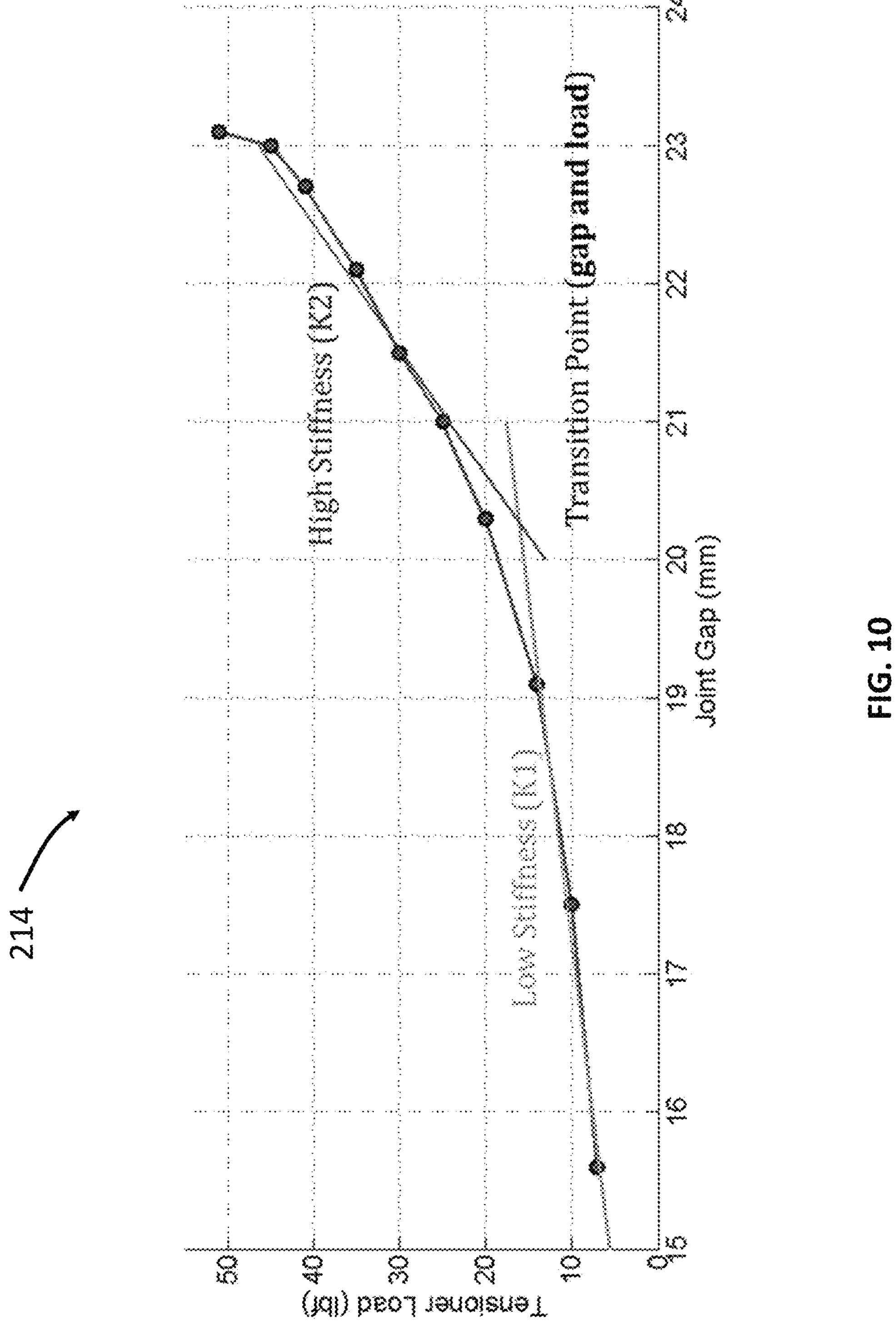
FIG. 10 is a graph showing joint gap versus tensioner load to identify a transition point.
Figure 13:
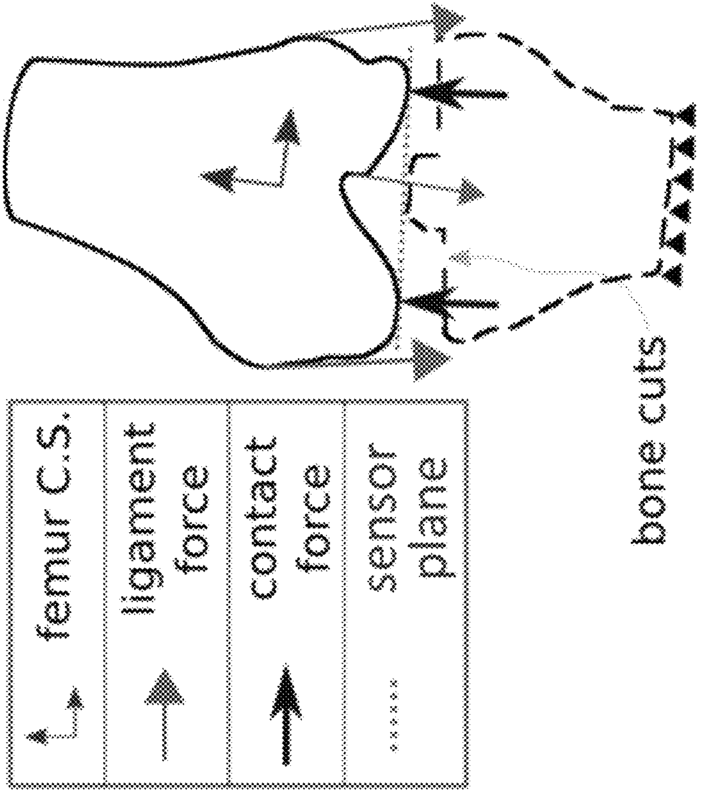
FIG. 13 is a schematic drawing showing a knee joint with various loading and resultant forces on account of same.
Figure 15:
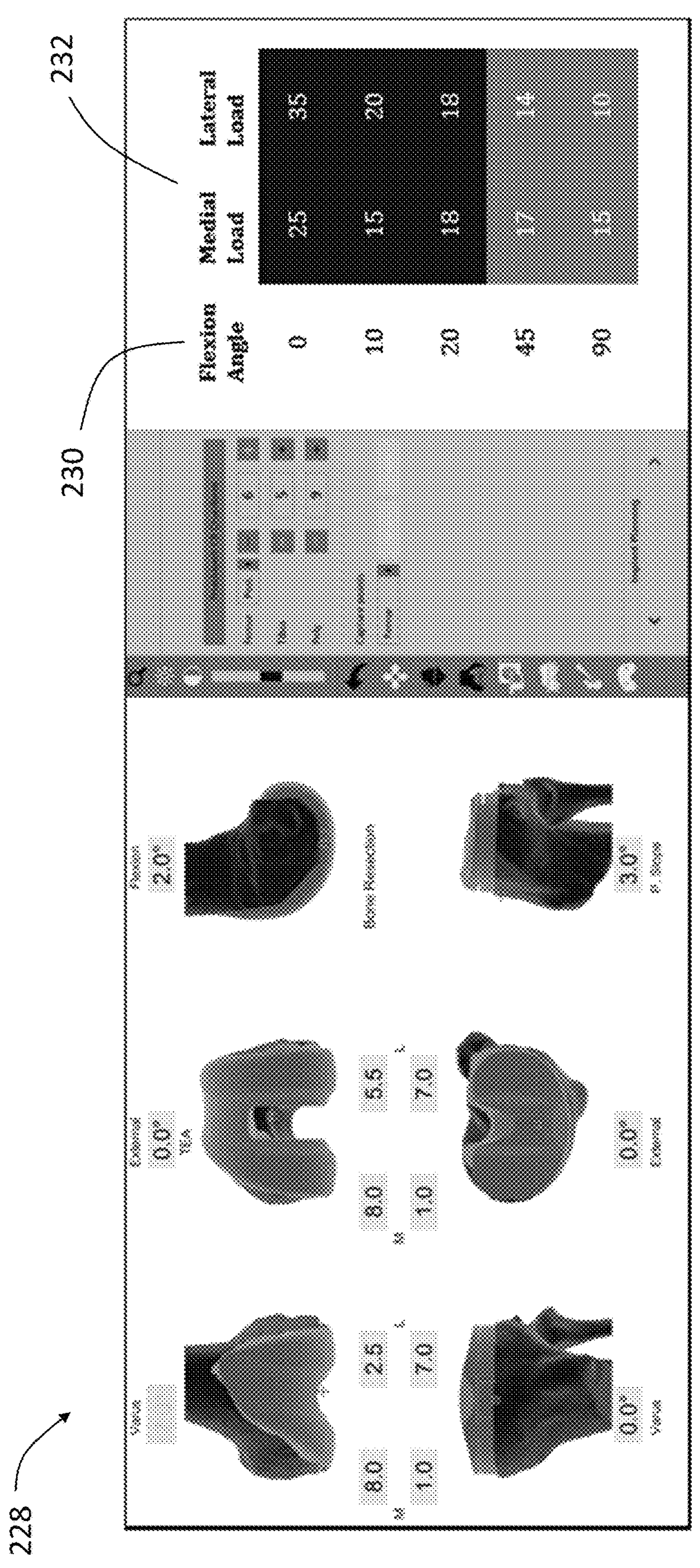
FIG. 15 is a schematic view of lateral and medial load changes with reference to the design of experiment matrix of FIG. 14.

A step 3 206 includes creating a real-time planning parameter design of experiment matrix (DOE) 226 as shown in FIG. 14. DOE matrix 226 can include tibial and femoral planning parameters such as insert thickness, slope, valgus-varus, external rotation, translations, external rotation, etc. A surgeon can choose a center point of DOE matrix 226 as mechanical, anatomical or user defined and change the bounds of DOE if necessary. Each experiment can be simulated using calibrated virtual model 208. Compartment load 230 at each flexion angle 232 for each case in the DOE can be displayed and compared in display 228 as shown in FIG. 15. Virtual model 228 can be simulated to show various loading types and the resultant forces corresponding to these loads as shown in load and force diagram 220 in FIG. 13. Transition points for joint gap and tensioner load can be identified by plotting a graph 214 from the results of a virtual model 228 simulation as shown in FIG. 10.

A step 4 208 includes planning parameters for a preferred surgical outcome. Based on the DOE results, a color-coded planning parameter based on load balance is used to expand the threshold or modify the target loads and visualize feasible cases. When visualizing one of the feasible cases, surgeons can adjust planning parameters live and see how the medial and lateral load change based on the DOE runs shown in FIG. 10.

While the virtual ligament modeling of the present disclosure is generally discussed with reference to a knee, it should be understood that the virtual ligament modeling can be utilized in any joint procedure conducted manually or robotically or any combination thereof. Output from virtual model 228 can be utilized in conjunction with balance algorithm 100 to simulate input data provided to the balancer algorithm.

Outcome Prediction

Figure 16:
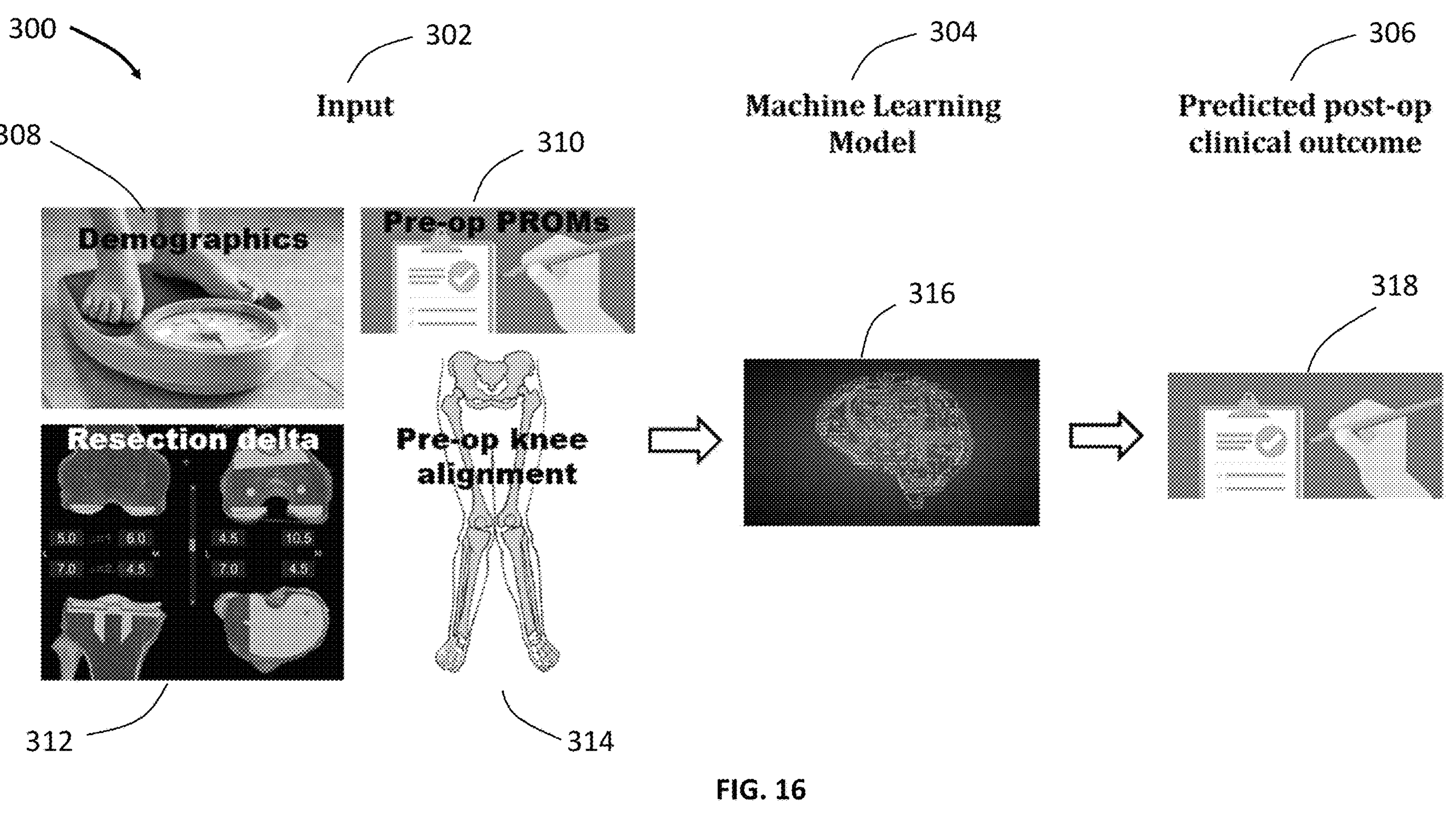
FIG. 16 is a schematic drawing showing a knee joint alignment outcome prediction model.

Referring now to FIG. 16, there is shown a schematic drawing of knee joint alignment outcome prediction model 300 according to an embodiment of the present disclosure. Various input data 308 such as patient demographic information 308, bone resection data 312, preoperative Patient-Reported Outcome Measures ("PROMS") 314, preoperative knee alignments 314, etc. is provided to a machine learning model 304 such as neural network 316 to compute a predicted postoperative clinical outcome 306 in various reporting formats 318. Outcome prediction model 300 can utilize various prediction algorithms ranging from a rule-based algorithm to a full-fledged AI solution. The prediction algorithm can include a positive outcome probability score, where the selected outcome is dichotomized into positive and negative outcome according to a threshold derived from scientific literature and the score (e.g., value ranging between 0 and 1 or 0 and 100) refers to the likelihood of the patient having a positive post-op outcome. Alternatively, a Minimal Clinically Important Difference ("MCID") probability score can be used, where the score refers to the likelihood of measuring a change in the outcome from pre-op to post-op equal or greater than the MCID. An MCID can be defined as the smallest change in a treatment outcome that an individual patient would identify as important. In other embodiments, a post-op outcome estimate can be used to identify an absolute number representing the estimate of the post-op selected outcome for the patient.

Outcome prediction model can generate various outcome predictors such as clinical outcomes, financial outcomes, general or joint-specific patient reported outcome measure, functional outcomes, etc. Clinical outcomes can include length of stay, (all-cause or TKA-related) re-admission, risk for revision, TKA-related infection, etc. Financial outcomes can include pharmacy utilization, healthcare utilization, healthcare expenditures, etc. General or joint-specific PROMs can include EQ-5D, Forgotten Joint Score ("FJS"), Knee Injury and Osteoarthritis Outcome Score for Joint Replacement ("KOOS JR"), Pain VAS score WOMAC (The Western Ontario and McMaster Universities Arthritis Index), SF-12/SF-36, Oxford Knee Score (OKS), satisfaction, etc. Functional outcomes can include range of motion ("ROM"), etc. The outcome predictors described herein can used to identify inputs and/or weighting priority for balance algorithm 100.

Figure 24:
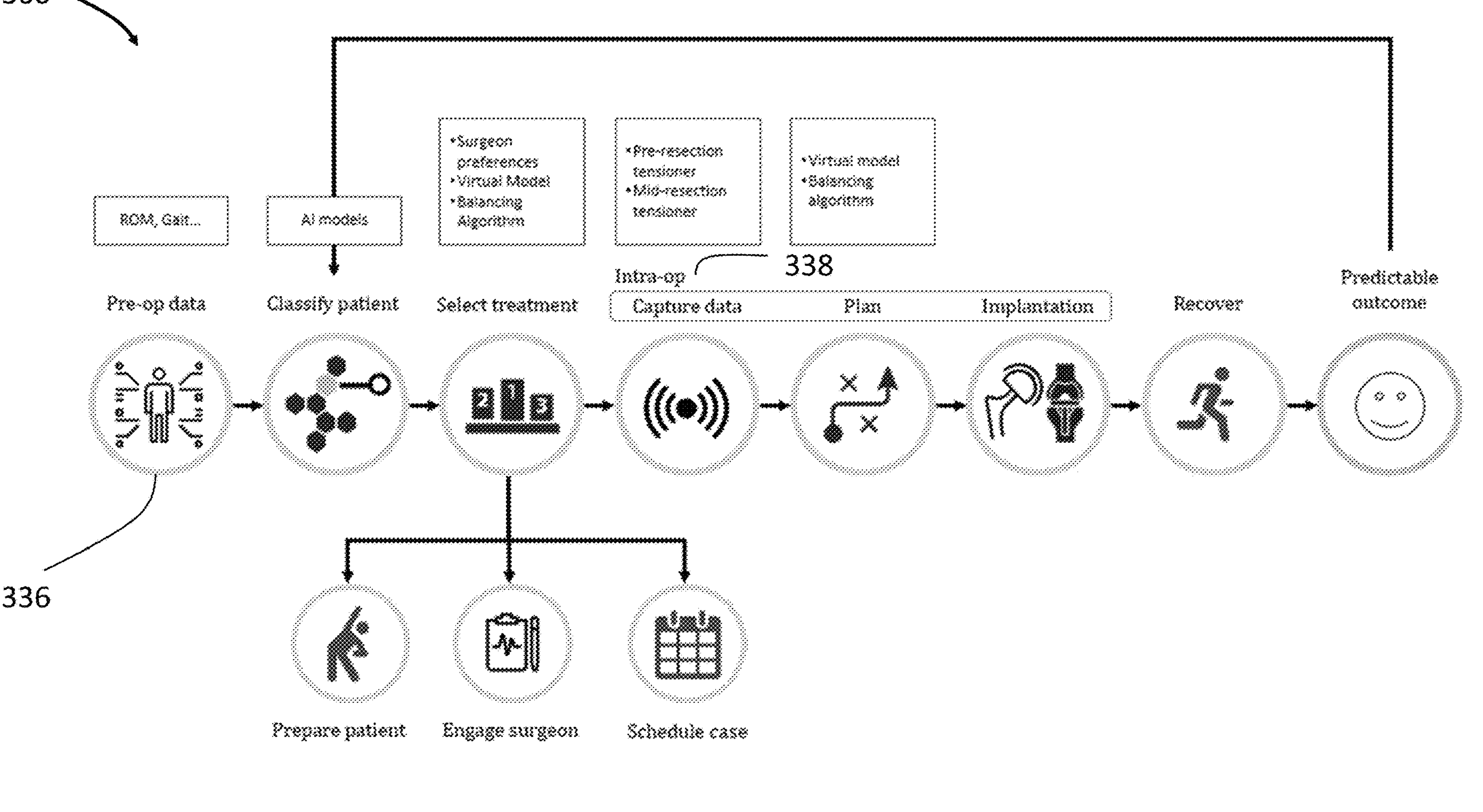
FIG. 24 is another schematic drawing of the knee joint alignment outcome prediction model.

FIG. 24 shows another schematic drawing of the various modules of knee joint alignment outcome prediction model 300. Pre-operative information 336 can include patient demographics such as height, weight, gender, age, etc. Pre-op conditions can include any of the outcomes measured before surgery more fully described above. Anatomical measures can include anatomical hip-knee-ankle angle ("aHKA"), medial proximal tibial angle ("MPTA"), lateral distal femoral angle ("LDFA"), etc. Both the pre-op and post-op values for the above-mentioned anatomical measures as well as combination of these values can be used. For example, the joint line can be represented as the sum of MPTA and LDFA, or HKA as the difference between MPTA and LDFA as shown in graph 329 of FIG. 20. These values are then used as coordinates on a 2D plane to describe both the pre and post-op patient's knee anatomy. Subsequently, the amount and direction—i.e., angle between the segment connecting the two points on the 2D plane and the y-axis, of the pre- to post-op change is computed and used as a predictor.

Intra-operative information 338 can include flexion and extension gaps, soft tissue release information, resection depth delta, difference between medial and lateral bone resection depth for distal femur (Δ dist.), difference between medial and lateral bone resection depth for posterior femur (Δ post), difference between lateral and medial bone resection depth for proximal tibia (Δ tib), medial and lateral loads in flexion and extension. Surgeon philosophy or preference regarding mechanical alignment, kinematic alignment, mechanical alignment+intra-op ligament balancing, kinematic alignment+intra-op ligament balancing, tibia vs. femur cut first, etc. can also be input to prediction model 300. Alternatively, simulated data from virtual ligament model 218 can be used as input to prediction model 300.

Figure 18:
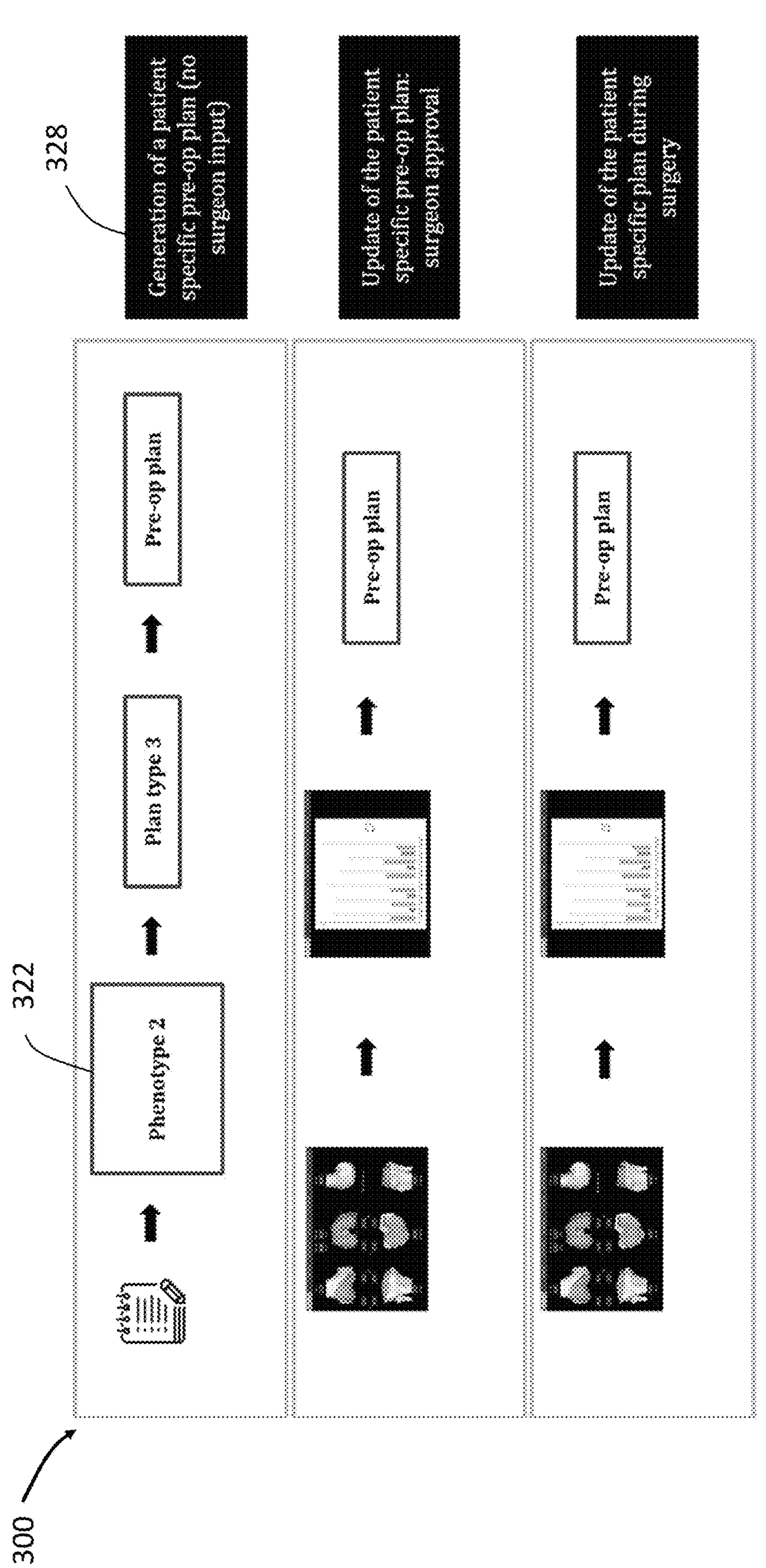
FIG. 18 is a schematic drawing showing another embodiment of the treatment clustering module of the knee joint alignment outcome prediction model of FIG. 16.
Figure 19:
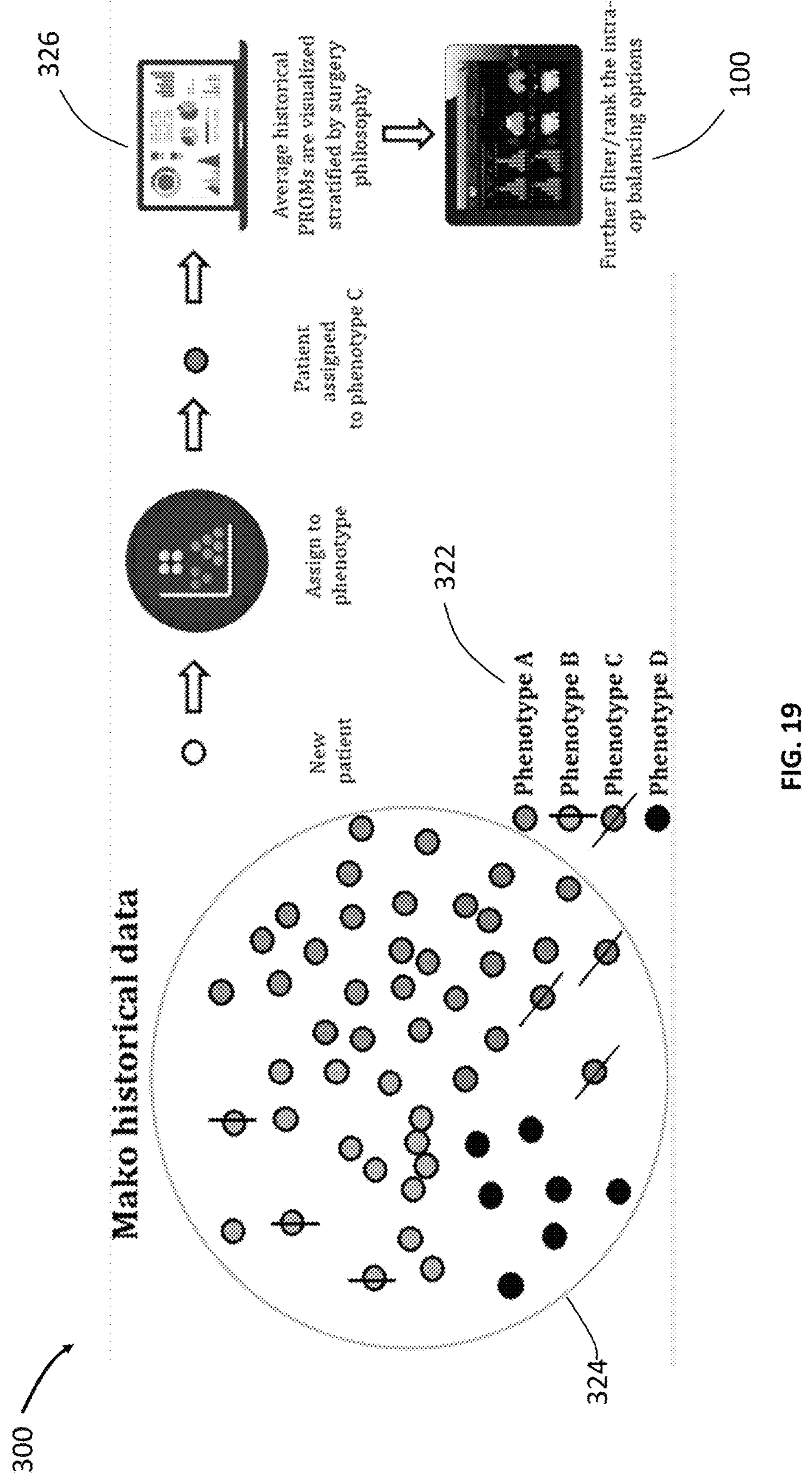
FIG. 19 is a schematic drawing showing a knee joint alignment outcome prediction model according to another embodiment of the present disclosure.

Referring now to FIG. 17, there is shown a schematic drawing of a clustering module 320 of knee joint alignment outcome prediction model 300 according to an embodiment of the present disclosure. Pre-op information is used to cluster patients in different sub-cohorts based on a selected similarity measure. For example, various measures can be specified bases on scientific literature and applied to a particular case set. Initially the patients' clustering 324 can be based on historical data as shown in FIG. 19 where each patient is identified under a particular phenotype 322, which allows the system to retrieve average historical PROMs for the particular phenotype 322. Depending on the identified phenotype, a patient specific-preoperative plan without any surgeon input can be generated by the system 328 as shown in FIG. 18. A surgeon can update patient-specific plan 328 preoperatively or intraoperatively. Each new case selected by a surgeon is added to the dataset thereby case history influences future analysis and outputs. Each sub-cohort is considered a phenotype. Every new patient is assigned to a phenotype and the surgeon is presented with descriptive statistics referring to the selected phenotype to enable informed decisions. Information such as historical average post-op outcomes, most used intra-op parameters are shown. Information can be ranked to identify preferred solutions to a particular geometrical problem with multiple solution—for example, to identify implant position 334 and orientation 330, implant variable 332, surgeon preference, etc. as shown in FIGS. 21-23. Balancer algorithm 100 can be used in conjunction with knee joint alignment outcome prediction model 300 to identify the preferred solution.

Figure 25:
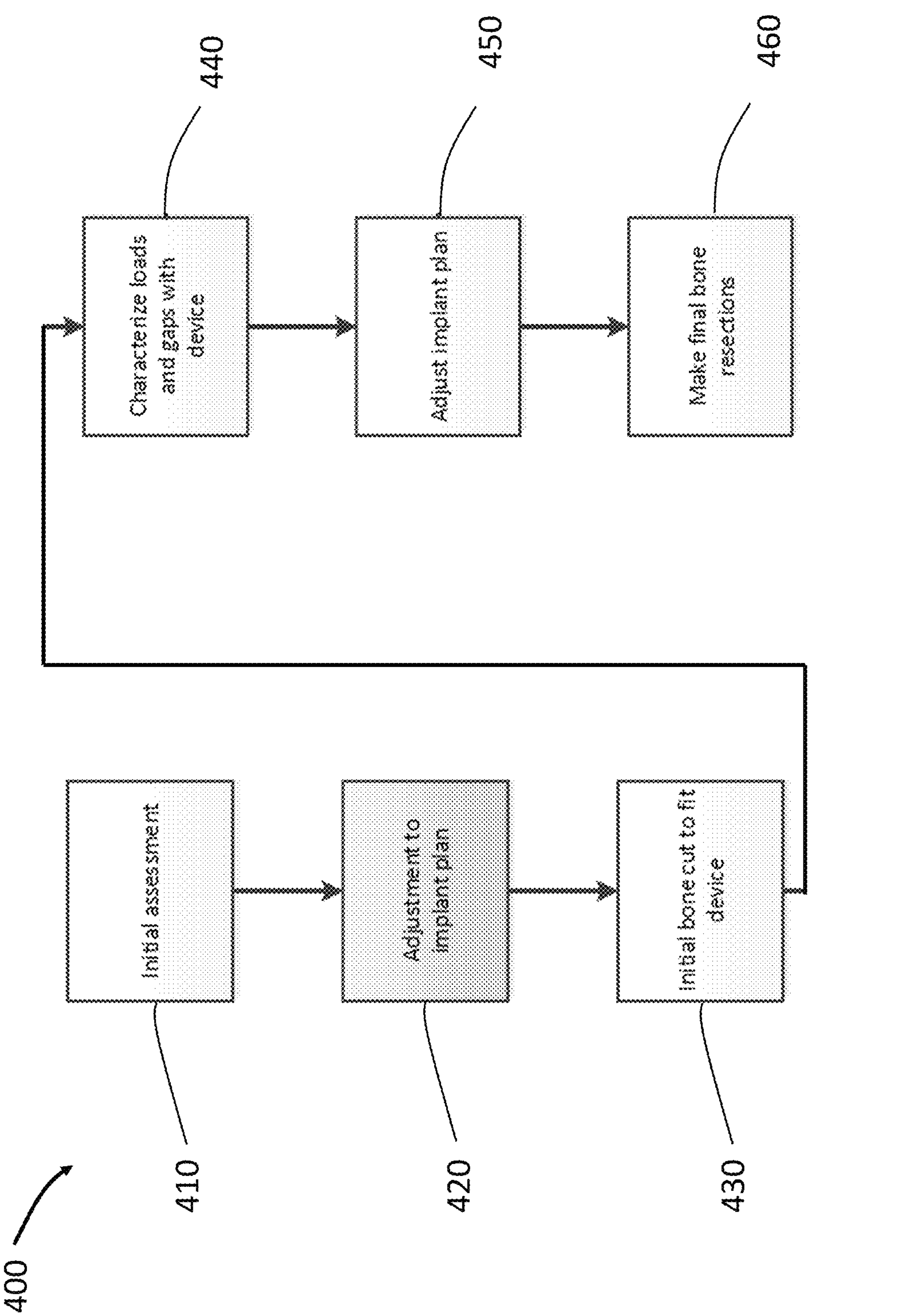
FIG. 25 is a flowchart illustrating the various steps for locating femoral and tibial components on a knee joint according to an embodiment of the present disclosure.

FIG. 25 shows a flowchart illustrating a method 400 for locating femoral and tibial components on a knee joint according to an embodiment of the present disclosure. According to this method, femoral and tibial components may be located utilizing a 10-0-90-degree knee flexion/extension workflow with a tensor. An initial assessment is performed in step 410 is first performed to remove osteophytes, collect native and sagittal alignment of the knee joint. Tissue releases can be performed depending on measured displacement of knee. Maximum gaps are then evaluated at 0 and 90 deg.

Adjustments to the implant plan are performed in step 420. The tibial component can be rotated (varus/valgus) and translate in a proximal-distal direction to maximize tibial motion and minimize femur motion, and maintain femur concentricity. An initial bone cut to fit the tensor is then performed in step 430. A proximal tibial cut and distal and posterior femoral cuts are made. This is followed by insertion a tensor to check for high loads which may be higher than a predetermined patient specific target. If high loads are detected, or if the tensor does not fit in the joint, the tibia can be recut.

In a step 430, knee loads and gaps are assessed. Loads at 10 deg flexion is first applied. Next, the joint is moved to full extension to determine if 0 deg limb flexion is achieved. Capture pose at 0 deg to determine flexion angle. The joint is then move to 90 degrees and subject to the same loads. Knee position is captured at this stage. Alternatively, this step can be performed with virtual model 218 as more fully described above.

Depending on the results of step 430, the implant plan cane be adjusted at a step 440. If the adjusted component position falls outside a desired alignment boundary, a soft tissue release can be considered. Steps of method 400 can be repeated until the final component positions fall within the desired range. Once this is achieved, final bone resections can be made in step 450.

Furthermore, although the invention disclosed herein has been described with reference to particular features, it is to be understood that these features are merely illustrative of the principles and applications of the present invention. While the embodiments of the present disclosure are generally described with reference to the knee joint, it should be understood that these embodiments can be used for all other joints including the hip and shoulder. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A method of determining femoral and tibial implant angulations for a knee arthroplasty procedure, the method comprising the steps of:

inputting preoperative knee data to an input screen of a computing device, the preoperative knee data including initial femoral and tibial resection depths;

selecting targeted postoperative knee data using the input screen, the targeted postoperative knee data including targeted implant angulations and implant angulation ranges, the targeted implant angulations including the femoral implant angulation with reference to a femur, and the tibial implant angulation with reference to a tibia;

determining a plurality of planned implant angulations using a balancer algorithm of the computing device based on preoperative knee data and intraoperative knee data, the plurality of planned implant angulations being within the implant angulation ranges, scoring the plurality of planned implant angulations using the balancer algorithm based on a weighted combination of medial epicondylar drift, lateral column length, proximity to target angulations and gap deviations from ideal gaps;

ranking the plurality of planned implant angulations based on the scoring to select final implant angulations; and displaying final implant angulations from the plurality of planned implant angulations on an output screen of the computing device, wherein the final implant angulations are within the targeted postoperative implant angulation ranges.

2. The method of claim 1, wherein the step of selecting the final implant angulations is performed in real time in response to any change of the targeted postoperative knee data.

3. The method of claim 2, wherein the final implant angulations include a final femoral implant angulation, a final femoral implant rotation, and a final tibial implant angulation.

4. The method of claim 2, wherein the preoperative knee data includes initial femoral and tibial resection depths.

5. The method of claim 4, wherein the initial femoral and tibial resection depths include an initial distal medial femoral resection depth, an initial distal lateral femoral resection depth, an initial posterior medial femoral resection depth, and an initial posterior lateral femoral resection depth.

6. The method of claim 5, wherein the initial femoral tibial resection depths include an initial medial tibial resection depth and an initial proximal lateral tibial resection depth.

7. The method of claim 5, wherein the preoperative knee data includes initial femoral implant angulation and rotation.

8. The method of claim 7, wherein the preoperative knee data includes an initial tibial implant angulation.

9. The method of claim 8, wherein the preoperative knee data includes initial medial and lateral extension and flexion gaps.

10. The method of claim 9, wherein the preoperative knee data includes initial limb extension and flexion angles.

11. The method of claim 5, wherein the targeted postoperative knee data includes a targeted postoperative femoral implant angulation range and a targeted postoperative femoral implant rotation range.

12. The method of claim 11, wherein the targeted postoperative knee data includes a targeted postoperative tibial implant angulation range.

13. The method of claim 12, wherein the targeted postoperative knee data includes targeted postoperative medial and lateral extension gap ranges.

14. The method of claim 13, wherein the targeted postoperative knee data includes targeted postoperative limb extension and flexion angle ranges.

15. The method of claim 12, wherein the step of determining the plurality of planned implant angulations includes the steps of:

iteratively calculating gaps falling between targeted postoperative gap ranges;

iteratively calculating tibial implant angulations falling between the targeted postoperative tibial angulation range;

iteratively calculating femoral resections depths falling between the initial femoral resection depths, and iteratively calculating a required soft tissue release and a required quadrant for the release.

16. The method of claim 15, wherein the medial epicondylar drift is calculated from a femoral component shift.

17. The method of claim 16, wherein the targeted postoperative knee data includes the required soft tissue release in a medial extension quadrant, a lateral extension quadrant, a medial flexion quadrant or a lateral flexion quadrant.

18. The method of claim 1, wherein the balancer algorithm generates the plurality of planned implant angulations for a single patient intra-operatively during the knee arthroplasty procedure.

19. The method of claim 1, wherein the plurality of planned implant angulations comprises a list of solutions, wherein the balancer algorithm displays the plurality of planned implant angulations on the output screen in order of their respective scores from lowest to highest.

* * * * *